United States Patent [19]
Crowell et al.

[11] Patent Number: 6,046,227
[45] Date of Patent: Apr. 4, 2000

[54] SELECTIVE β3 ADRENERGIC AGONISTS

[75] Inventors: Thomas Alan Crowell; Charles David Jones; Anthony John Shuker, all of Indianapolis, Ind.

[73] Assignee: Eli Lilly and Company, Indianapolis, Ind.

[21] Appl. No.: 09/206,107

[22] Filed: Dec. 4, 1998

Related U.S. Application Data

[63] Continuation of application No. 09/204,372, Dec. 2, 1998
[60] Provisional application No. 60/067,599, Dec. 5, 1997.

[51] Int. Cl.$^7$ .................. A61K 31/415; C07D 231/18
[52] U.S. Cl. .................. 514/407; 544/140; 544/219; 544/237; 546/276.1; 546/291; 546/300; 546/340; 548/238; 548/252; 548/253; 548/312.4; 548/343.1; 548/365.7; 548/369.4; 548/370.1
[58] Field of Search .................. 544/140; 548/369.4, 548/370.1; 514/407

[56] References Cited

U.S. PATENT DOCUMENTS

| | | |
|---|---|---|
| 3,920,691 | 11/1975 | Wasson et al. . |
| 4,032,575 | 6/1977 | Ikezaki et al. . |
| 4,140,789 | 2/1979 | Jaeggi et al. . |
| 4,235,919 | 11/1980 | Berthold . |
| 4,288,452 | 9/1981 | Sombroek et al. . |
| 4,309,443 | 1/1982 | Smith et al. . |
| 4,310,527 | 1/1982 | Jaeggi et al. . |
| 4,338,333 | 7/1982 | Ainsworth et al. . |
| 4,346,093 | 8/1982 | Friebe et al. . |
| 4,367,235 | 1/1983 | Ross et al. . |
| 4,385,066 | 5/1983 | Ainsworth et al. . |
| 4,391,826 | 7/1983 | Mills et al. . |
| 4,396,627 | 8/1983 | Ainsworth et al. . |
| 4,432,993 | 2/1984 | Ferris . |
| 4,478,849 | 10/1984 | Ainsworth et al. . |
| 4,497,813 | 2/1985 | Ostermayer et al. . |
| 4,503,067 | 3/1985 | Wiedemann et al. . |
| 4,513,001 | 4/1985 | Joannic et al. . |
| 4,636,511 | 1/1987 | Ostermayer et al. . |
| 4,652,679 | 3/1987 | Alig et al. . |
| 4,697,022 | 9/1987 | Leinert . |
| 4,727,067 | 2/1988 | Ostermayer et al. . |
| 4,751,246 | 6/1988 | Philion . |
| 4,772,631 | 9/1988 | Holloway et al. . |
| 4,892,886 | 1/1990 | Alig et al. . |
| 4,940,800 | 7/1990 | Bertolini et al. . |
| 4,960,783 | 10/1990 | Bonse et al. . |
| 4,977,148 | 12/1990 | Holloway et al. . |
| 5,013,761 | 5/1991 | Beedle et al. . |
| 5,064,863 | 11/1991 | Alig et al. . |
| 5,166,218 | 11/1992 | Alig et al. . |
| 5,254,595 | 10/1993 | Guzzi et al. . |
| 5,321,036 | 6/1994 | Sher . |
| 5,393,772 | 2/1995 | Yue et al. . |
| 5,420,294 | 5/1995 | Beedle et al. . |
| 5,453,436 | 9/1995 | Ohlstein . |
| 5,488,151 | 1/1996 | Baroni et al. . |
| 5,534,640 | 7/1996 | Tegeler et al. . |
| 5,541,197 | 7/1996 | Fisher et al. . |
| 5,541,204 | 7/1996 | Sher et al. . |
| 5,561,142 | 10/1996 | Fisher et al. . |
| 5,574,164 | 11/1996 | Tegeler et al. . |
| 5,776,983 | 7/1998 | Washburn et al. . |

FOREIGN PATENT DOCUMENTS

| | | |
|---|---|---|
| 0 040 000 | 11/1981 | European Pat. Off. . |
| 0 052 963 | 6/1982 | European Pat. Off. . |
| 0 061 907 | 10/1982 | European Pat. Off. . |
| 0 063 004 | 10/1982 | European Pat. Off. . |
| 0 066 351 | 12/1982 | European Pat. Off. . |
| 0 068 669 | 1/1983 | European Pat. Off. . |
| 0 070 134 | 1/1983 | European Pat. Off. . |
| 0 082 665 | 6/1983 | European Pat. Off. . |
| 0 089 154 | 9/1983 | European Pat. Off. . |
| 0 091 749 | 10/1983 | European Pat. Off. . |
| 0 095 827 | 12/1983 | European Pat. Off. . |
| 0 099 707 | 2/1984 | European Pat. Off. . |
| 1 102 213 | 3/1984 | European Pat. Off. . |
| 0 171 702 | 2/1986 | European Pat. Off. . |
| 0 196 849 | 10/1986 | European Pat. Off. . |
| 0 211 721 | 2/1987 | European Pat. Off. . |

(List continued on next page.)

OTHER PUBLICATIONS

Tejani–Butt and Brunswick. "Synthesis an β–Adrenergic Receptor Blocking Potency of 1–(Substituted amino)–3–(4–indolyloxy) propan–2–ols" *J. Med. Chem* 29:1524–1527 (1986).

Bürgisser, et al. "Alternative Explanation for the Apparent 'Two Step' Binding Kinetics of High–Affinity Racemic Antagonist Radioligands" *Molecular Pharmacology* 19:509–512 (1981).

Marinetti, et al. "Beta–Adrenergic Receptors of Human Leukocytes" *Biochemical Pharmacology* 32(13):2033–2043 (1983).

Howe, et al. "Selective b3–adrenergic agonists of brown adipose tissue and thermogenesis" *Chemical Abstracts* 117: 40209r (1992).

Jimenez, et al. "1–Thymoxy–2–propanolamines" *Chemical Abstracts* 86:29468v (1977).

Izquiero Sanjose, et al. "Morpholine derivative and its salts" *Chemical Abstracts* 90:186971d (1979).

*Primary Examiner*—Robert W. Ramsuer
*Attorney, Agent, or Firm*—Steven G. Davis

[57] ABSTRACT

The present invention is in the field of medicine, particularly in the treatment of Type II diabetes and obesity. More specifically, the present invention relates to selective β$_3$ receptor agonists useful in the treatment of Type II diabetes and obesity. The invention provides compounds and methods of treating type II diabetes and obesity, comprising administering to a mammal in need thereof compounds of the Formula I:

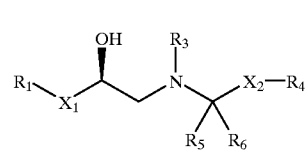

23 Claims, No Drawings

FOREIGN PATENT DOCUMENTS

| | | |
|---|---|---|
| 0 236 624 | 9/1987 | European Pat. Off. . |
| 0 328 251 A3 | 1/1989 | European Pat. Off. . |
| 0 345 056 A2 | 6/1989 | European Pat. Off. . |
| 0 386 920 | 9/1990 | European Pat. Off. . |
| 0 455 006 A2 | 6/1991 | European Pat. Off. . |
| 0 436 435 A1 | 10/1991 | European Pat. Off. . |
| 0 500 443 A1 | 8/1992 | European Pat. Off. . |
| 0 565 317 A1 | 10/1993 | European Pat. Off. . |
| 0 611 003 A1 | 3/1994 | European Pat. Off. . |
| 0 659 737 A2 | 12/1994 | European Pat. Off. . |
| 0 642 787 A2 | 3/1995 | European Pat. Off. . |
| 0 687 472 A2 | 12/1995 | European Pat. Off. . |
| 0 714 663 A2 | 6/1996 | European Pat. Off. . |
| 40 40 186 A1 | 6/1991 | Germany . |
| 636 856 A5 | 6/1983 | Switzerland . |
| 1 391 828 | 4/1975 | United Kingdom . |
| 1 532 380 | 11/1978 | United Kingdom . |
| 1 549 945 | 8/1979 | United Kingdom . |
| 1 571 231 | 9/1980 | United Kingdom . |
| WO 92/18461 | 10/1992 | WIPO . |
| WO 93/22277 | 11/1993 | WIPO . |
| WO 94/03425 | 2/1994 | WIPO . |
| WO 94/02493 | 3/1994 | WIPO . |
| WO 94/29290 | 12/1994 | WIPO . |
| WO 95/04047 | 9/1995 | WIPO . |
| WO 95/01170 | 12/1995 | WIPO . |
| WO 96/04233 A1 | 2/1996 | WIPO . |
| WO 96/04243 | 2/1998 | WIPO . |

SELECTIVE β3 ADRENERGIC AGONISTS

RELATED APPLICATIONS

This application claims the benefit of U.S. Ser. No. 09/204,372 filed on Dec. 2, 1998, which claims the benefit of U.S. Provisional Application Ser. No. 60/067,599, filed on Dec. 5, 1997, the entire teachings of which are incorporated herein by reference.

FIELD OF INVENTION

The present invention is in the field of medicine, particularly in the treatment of Type II diabetes and obesity. More specifically, the present invention relates to selective $\beta_3$ adrenergic receptor agonists useful in the treatment of Type II diabetes and obesity.

BACKGROUND OF THE INVENTION

The current preferred treatment for Type II, non-insulin dependent, diabetes as well as obesity is diet and exercise, with a view toward weight reduction and improved insulin sensitivity. Patient compliance, however, is usually poor. There are no currently approved medications that adequately treat either Type II diabetes or obesity. The invention described herein is directed toward an effective and timely treatment for these serious diseases.

One recently recognized therapeutic opportunity involves the relationship between adrenergic receptor stimulation and anti-hyperglycemic effects. Compounds that act as $\beta_3$ adrenergic receptor agonists have been shown to exhibit a marked effect on lipolysis, thermogenesis, and serum glucose levels in animal models of Type II diabetes.

The $\beta_3$ receptor, which is found in several types of human tissue including human fat tissue, has roughly 50% homology to the $\beta_1$ and $\beta_2$ receptor subtypes yet is considerably less abundant. The importance of the $\beta_3$ receptor is a relatively recent discovery since the amino-acid sequence of the human receptor was only elucidated in the late 1980's. A large number of publications have appeared in recent years reporting success in discovery of agents that stimulate the $\beta_3$ receptor. Despite these recent developments there remains a need to develop a selective $\beta_3$ receptor agonist which has both high intrinsic activity and minimal agonist activity against the $\beta_1$ and $\beta_2$ receptors.

SUMMARY OF INVENTION

The present invention provides a novel compound represented by Formula (I) below and methods of treating Type II diabetes, treating obesity, and stimulating the $\beta_3$ receptor which comprise administering to a patient in need thereof a compound described by Formula I below.

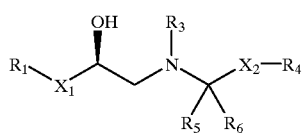

(I)

wherein:

$X_1$ is —$OCH_2$—, —$SCH_2$—, or a bond;

$R_1$ is a heterocycle of the formula:

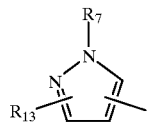

$R_2$ and $R_3$ are independently hydrogen, $C_1$–$C_4$ alkyl, or aryl;

$R_4$ is an optionally substituted heterocycle or a moiety selected from the group consisting of:

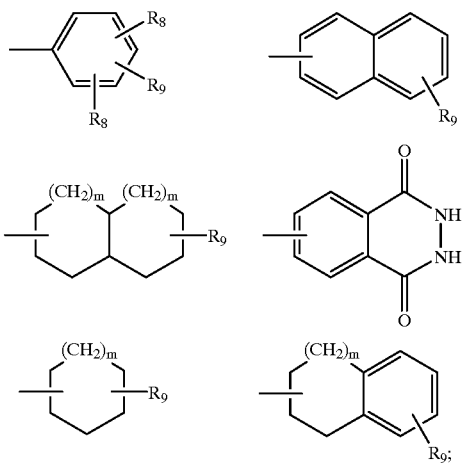

$X_2$ is a bond, or a 1 to 5 carbon straight or branched alkylene;

$R_5$ is hydrogen or $C_1$–$C_4$ alkyl;

$R_6$ is hydrogen or $C_1$–$C_4$ alkyl;

or $R_5$ and $R_6$ combine with the carbon to which each is attached to form a $C_3$–$C_6$ cycloalkyl;

or $R_6$ combines with $X_2$ and the carbon to which each is attached to form a $C_3$–$C_8$ cycloalkyl;

or $R_6$ combines with $X_2$, $R_4$, and the carbon to which each is attached to form:

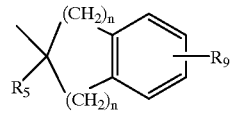

provided that $R_5$ is hydrogen;

$R_7$ is hydrogen, hydroxy, cyano, oxo, $CO_nR_2$, $CONHR_2$, $C_1$–$C_4$ alkyl, $C_1$–$C_4$ alkoxy, $C_1$–$C_4$ haloalkyl, $C_1$–$C_4$ optionally substituted alkyl, $(CH_2)_n$ aryl, $(CH_2)_n$heterocycle, $(CH_2)_n$ optionally substituted aryl, or $(CH_2)_n$ optionally substituted heterocycle;

$R_8$ is independently hydrogen, halo, or $C_1$–$C_4$ alkyl;

$R_9$ is halo, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNHR_2$, $CSNR_{11}R_{12}$, $SO_2R_2$, $SOR_2$, $NR_{11}R_{12}$, optionally substituted aryl, optionally substituted heterocycle, or $C_2$–$C_4$ alkenyl substituted with CN, $CO_2R_2$, or $CONR_{11}R_{12}$;

$R_{10}$ is $C_1$–$C_4$ alkyl, $C_1$–$C_4$ haloalkyl, $(CH_2)_nC_3$–$C_8$ cycloalkyl, $(CH_2)_n$aryl, $(CH_2)_n$heterocycle, $(CH_2)_nC_3$–$C_8$ optionally substituted cycloalkyl, $(CH_2)_n$ optionally substituted aryl, or $(CH_2)_n$ optionally substituted heterocycle;

$R_{11}$ and $R_{12}$ are independently hydrogen, $C_1$–$C_4$ alkyl, aryl, $(CH_2)_n$aryl, or combine with the nitrogen to which each is bound to form morpholinyl, piperidinyl, pyrrolidinyl, or piperazinyl;

$R_{13}$ is hydrogen, halo, aryl, or $C_1$–$C_4$ alkyl;

m is 0 or 1;

n is 0, 1, 2, or 3;

or a pharmaceutically acceptable salt thereof.

The present invention also provides novel pharmaceutical formulations of the compounds of Formula I.

The present invention also provides a novel compound of Formula (I) wherein all variables except $R_4$, $R_6$ and $R_9$ are as described above. $R_4$ additionally includes thiophene optionally substituted with $R_9$; $R_9$ additionally includes $NR_2SO_2R_2$ and $SO_2NR_{11}R_{12}$; and $R_6$ is: 1) hydrogen or $C_1$–$C_4$ alkyl; 2) $R_5$ and $R_6$ combine with the carbon to which each is attached to form a $C_3$–$C_6$ cycloalkyl; 3) $R_6$ combines with $X_2$ and the carbon to which each is attached to form a Z or Z-$CH_2$, wherein Z is a $C_3$–$C_8$ cycloalkyl attached to the nitrogen atom in Formula (I); or 4) $R_6$ combines with $X_2$, $R_4$, and the carbon to which each is attached to form:

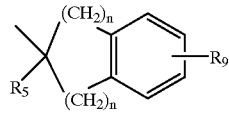

provided that $R_5$ is hydrogen.

Also included are methods of stimulating beta 3 receptors in a mammal in need thereof and methods of treating a mammal with Type II diabetes or obesity using a compound represented by Formula (I), modified as described in the previous paragraph. The method comprises administering a pharmaceutically effective amount of said compound.

The compounds of Formula I are selective $\beta_3$ receptor agonists and as such are useful for treating Type II diabetes and obesity, as well as useful for stimulating the $\beta_3$ receptor. Therefore, the present invention also provides for methods of treating Type II diabetes and obesity, as well as a method of stimulating the $\beta_3$ receptor.

DETAILED DESCRIPTION OF THE INVENTION

For the purposes of the present invention, as disclosed and claimed herein, the following terms, as used herein, are defined below. As they relate to the present invention, the terms below may not be interpreted, individually or collectively, to describe chemical structures that are unstable or impossible to construct.

The term "halo" represents fluorine, chlorine, bromine, or iodine.

The term "$C_1$–$C_4$ alkyl" represents a cyclo, straight, or branched chain alkyl group having from one to four carbon atoms such as methyl, ethyl, n-propyl, isopropyl, cyclopropyl, n-butyl, isobutyl, sec-butyl, t-butyl, and the like. A "haloalkyl" is one such alkyl substituted with one or more halo atoms, preferably one to three halo atoms. An example of a haloalkyl is trifluoromethyl. An "alkoxy" is a alkyl group covalently bonded by an —O— linkage.

The term "1 to 5 carbon straight or branched alkylene" represents a one to five carbon, straight or branched, alky-lene moiety. A branched alkylene may have one or more points of branching. A 1 to 5 carbon straight or branched alkylene may optionally be unsaturated at one or more carbons. Thus, a 1 to 5 carbon straight or branched alkylene includes 1 to 5 carbon alkylene, alkenylene and alkylidene moieties. Examples include but are not intended to be limited to methylene, ethylene, propylene, butylene, —CH($CH_3$)$CH_2$—$CH(C_2H_5)CH_2$—, —CH($CH_3$)CH($CH_3$)—, —$CH_2C(CH_3)_2$—, —$CH_2CH(CH_3)CH_2$—, —$C(CH_3)_2CH$=, —CH=$CHCH_2$—, —CH=CH—, —$CH_2CH_2$—C=$CCH_2$—, and the like.

The "acyl" moiety, alone or in combination, is derived from an alkanoic acid containing from one to seven carbon atoms. The term "acyl" also includes moieties derived from an aryl carboxylic acid.

The term "aryl" represents an optionally substituted or unsubstituted phenyl or naphthyl. The term $(CH_2)_n$aryl is preferably benzyl or phenyl.

The term "optionally substituted" as used herein means an optional substitution of one to three, preferably one or two groups independently selected from halo, $C_1$–$C_4$ haloalkyl, hydroxy, carboxy, tetrazolyl, acyl, $COOR_2$, $CONR_{11}R_{12}$, $CONH(C_1$–$C_4$ alkoxy), cyano, $C_1$–$C_4$ alkoxy, $C_1$–$C_4$ alkyl, phenyl, benzyl, nitro, $NR_{11}R_{12}$, $NHCO(C_1$–$C_4$ alkyl), NHCO(benzyl), NHCO(phenyl), $SR_2$, $S(C_1$–$C_4$ alkyl), OCO ($C_1$–$C_4$ alkyl), $SO_2(C_1$–$C_4$ alkyl), or $SO_2$(phenyl); provided that such substitution does not entirely destroy biological activity, as defined in this specification.

$R_2$ and $R_3$ are independently hydrogen, $C_1$–$C_4$ alkyl, or aryl.

$R_{11}$ and $R_{12}$ are independently hydrogen, $C_1$–$C_4$ alkyl, or combine with the nitrogen to which each is bound to form morpholinyl, piperidinyl, pyrrolidinyl, or piperazinyl.

The term "heterocycle" represents a stable, optionally substituted or unsubstituted, saturated or unsaturated 5 or 6 membered ring, said ring having from one to four heteroatoms that are the same or different and that are selected from the group consisting of sulfur, oxygen, and nitrogen. When the heterocycle contains two adjacent carbon atoms, the adjacent carbon atoms may be structured to form a group of the formula —CH=CH—; provided that (1) when the heterocyclic ring contains 5 members, the heteroatoms comprise not more than two sulfur or two oxygen atoms but not both, and (2) when the heterocyclic ring contains 6 members and is aromatic; sulfur and oxygen are not present. The heterocycle may be attached at any carbon or nitrogen which affords a stable structure. Examples of heterocycles include, but are not intended to be limited to, pyrazole, pyrazoline, imidazole, isoxazole, triazole, tetrazole, oxazole, 1,3-dioxolone, thiazole, oxadiazole, thiadiazole, pyridine, pyrimidine, piperazine, morpholine, pyrazine, pyrrolidine, piperidine, oxazolidone, oxazolidinedione, imidazolidinone, and the like.

The term "leaving group" as used in the specification is understood by those skilled in the art. Generally, a leaving group is any group or atom that enhances the electrophilicity of the atom to which it is attached for displacement. Preferred leaving groups include but are not intended to be limited to p-nitrobenzene sulfonate, triflate, mesylate, tosylate, imidate, chloride, bromide, iodide, and the like.

The term "pharmaceutically effective amount", as used herein, represents an amount of a compound of the invention that is capable of stimulating the $\beta_3$ receptor in mammals. The particular dose of the compound administered according to this invention will, of course, be determined by the particular circumstances surrounding the patient, including the compound administered, the route of administration, the particular condition being treated, and similar considerations.

The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The term "treating," as used herein, describes the management and care of a patient for the purpose of combating the disease, condition, or disorder and includes the administration of a compound of the present invention to prevent the onset of the symptoms or complications, to alleviate the symptoms or complications, or to eliminate the disease, condition, or disorder.

The term "selective" means preferential agonism of the $\beta_3$ receptor over agonism of the $\beta_1$ or $\beta_2$ receptor. In general, the compounds demonstrate at least about a twenty fold differential (preferably over a 50 fold differential) in the dosage required to behave as an agonist to the $\beta_3$ receptor and the dosage required for equal agonism of the $\beta_1$ and $\beta_2$ receptors as measured in the Functional Agonist Assay as described hereinafter. The compounds demonstrate this differential across the range of doses. Thus, $\beta_3$ selective compounds behave as agonists for the $\beta_3$ receptor at much lower concentrations with lower toxicity by virtue of their minimal agonism of the other receptors.

As previously noted, the present invention provides a method of treating type II diabetes and obesity, comprising administering to a mammal in need thereof compounds of the Formula I.

Referring again to Formula I, preferred embodiments of the present invention are set out in the lettered paragraphs below.

(a) $R_7$ is hydrogen.
(b) $R_7$ is $C_1$–$C_4$ alkyl or $C_1$–$C_4$ alkoxy.
(c) $R_7$ is hydroxy, cyano, oxide, $CO_nR_2$, $CONHR_2$, $C_1$–$C_4$ alkyl, $C_1$–$C_4$ alkoxy, $C_1$–$C_4$ haloalkyl, $C_1$–$C_4$ optionally substituted alkyl, $(CH_2)_n$ aryl, $(CH_2)_n$heterocycle.
(d) $R_7$ is $CO_nR_2$ or $CONHR_2$.
(e) $R_7$ is $(CH_2)_n$ aryl or $(CH_2)_n$heterocycle.
(f) $R_7$ is hydroxy or oxo.
(f1) $R_1$ is

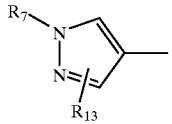

(g) $X_1$ is —$OCH_2$—, the oxygen of which is attached to $R_1$.
(h) $X_1$ is a bond.
(i) $R_3$ is methyl.
(j) $R_3$ is hydrogen.
(k) $R_5$ is methyl or ethyl.
(l) $R_6$ is methyl or ethyl.
(m) $R_5$ and $R_6$ are both methyl.
(m) $R_5$ and $R_6$ are both hydrogen.
(n) $X_2$ is isopropylene, methylene, or ethylene.
(n) $X_2$ is isopropylene
(o) $X_2$ is methylene.

(p) $X_2$ is ethylene.
(q) $R_4$ is

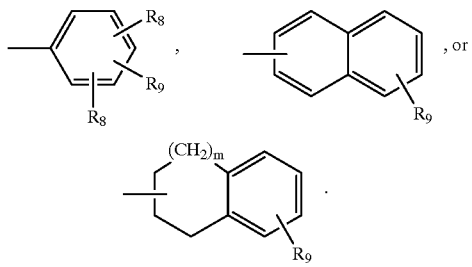

(r) $R_4$ is

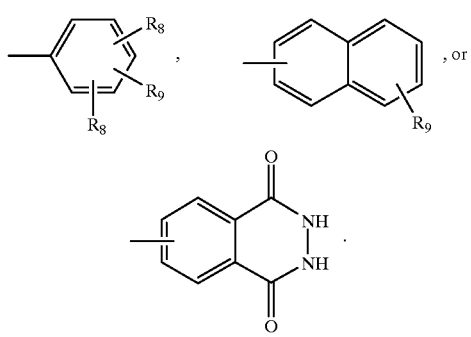

(s) $R_4$ is

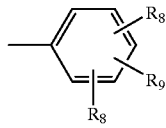

(t) $R_4$ is

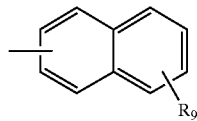

(u) $R_8$ is halo.
(v) $R_8$ is hydrogen.
(w) $R_8$ is halo, CN, $OR_{10}$, $C_1$–$C_4$ alkyl, $CO_2R_2$, $CONR_{11}R_{12}$, $CONH(C_1$–$C_4$ alkyl or $C_1$–$C_4$ alkoxy), $NR_2SO_2R_2$, $SO_2R_2$, $SO_2NR_{11}R_{12}$, $SOR_2$, optionally substituted aryl, optionally substituted heterocycle.
(x) $R_9$ is $CO_2R_2$, $CONR_{11}R_{12}$, $CONH(C_1$–$C_4$ alkyl or $C_1$–$C_4$ alkoxy), $NR_2SO_2R_2$, $SO_2R_2$, $SO_2NR_{11}R_{12}$, optionally substituted aryl, optionally substituted heterocycle, or $C_2$–$C_4$ alkenyl substituted with CN, $CO_2R_2$ or $CONR_{11}R_{12}$.
(y) $R_9$ is halo, CN, $C_1$–$C_4$ haloalkyl, $SR_2$, $CSNR_2$, $CSNR_{11}R_{12}$, $SO_2R_2$, $SO_2NR_{11}R_{12}$, $SOR_2$, optionally substituted aryl, optionally substituted heterocycle, or $C_2$–$C_4$ alkenyl substituted with CN, $CO_2R_2$ or $CONR_{11}R_{12}$.
(z) $R_9$ is $OR_{10}$, optionally substituted aryl, optionally substituted heterocycle, or $C_2$–$C_4$ alkenyl substituted with CN, $CO_2R_2$ or $CONR_{11}R_{12}$.
(aa) $R_9$ is $NR_2SO_2R_2$.
(bb) $R_9$ is CN.
(cc) $R_9$ is $CONR_{11}R_{12}$.
(dd) $R_9$ is $OR_{10}$.
(ee) $R_{10}$ is $(CH_2)_nC_3$–$C_8$ cycloalkyl, $(CH_2)_n$aryl, $(CH_2)_n$heterocycle, said aryl, $C_3$–$C_8$ cycloalkyl, or heterocycle being optionally substituted.

(ff) $R_{10}$ is $(CH_2)_nC_3-C_8$ cycloalkyl, $(CH_2)_n$heterocycle, said $C_3-C_8$ cycloalkyl, or heterocycle being optionally substituted.

(gg) $R_{10}$ is $(CH_2)_n$heterocycle said heterocycle being unsubstituted or optionally substituted.

(hh) $R_{10}$ is aryl.

(ii) $R_{10}$ is pyridyl.

(jj) $R_{10}$ is aryl substituted with $CONR_{11}R_{12}$, CN, $CO_2R_2$, or $NR_2SO_2R_2$.

(kk) $R_{10}$ is pyridyl substituted with $CONR_{11}R_{12}$, CN, $CO_2R_2$, or $NR_2SO_2R_2$.

(ll) $R_{10}$ is aryl substituted with $CONR_{11}R_{12}$.

(mm) $R_{10}$ is aryl substituted with CN.

(nn) $R_{10}$ is aryl substituted with $CO_2R_2$.

(oo) $R_{10}$ is aryl substituted with $NR_2SO_2R_2$.

(pp) $R_{10}$ is pyridyl substituted with $CONR_{11}R_{12}$.

(qq) $R_{10}$ is pyridyl substituted with CN.

(rr) $R_{10}$ is pyridyl substituted with $CO_2R_2$.

(ss) $R_{10}$ is pyridyl substituted with $NR_2SO_2R_2$.

(tt) $R_{13}$ is hydrogen.

(uu) $R_{13}$ is halo.

(vv) $R_{13}$ is $(CH_2)_n$aryl or $(CH_2)_n$heterocycle.

(ww) $R_{13}$ is $(CH_2)_n$aryl, $(CH_2)_n$heterocycle, or halo.

(xx) $R_{13}$ is $(CH_2)_n$aryl or $(CH_2)_n$heterocycle, wherein n is 0.

(yy) Preferred optional substitution is halo, $C_1-C_4$ haloalkyl, hydroxy, carboxy, tetrazolyl, acyl, $COOR_2$, $CONR_{11}R_{12}$, cyano, $C_1-C_4$ alkoxy, $C_1-C_4$ alkyl, phenyl, benzyl, nitro, $NR_{11}R_{12}$, NHCO(benzyl), $SO_2$ ($C_1-C_4$ alkyl), or $SO_2$(phenyl).

(zz) Other preferred optional substitution is halo, $C_1-C_4$ haloalkyl, hydroxy, carboxy, tetrazolyl, acyl, $COOR_2$, $CONR_{11}R_{12}$, cyano, $C_1-C_4$ alkoxy, $C_1-C_4$ alkyl, phenyl, nitro, or $NR_{11}R_{12}$.

(aaa) Other preferred optional substitution is halo, hydroxy, carboxy, acyl, $COOR_2$, $CONR_{11}R_{12}$, cyano, $C_1-C_4$ alkoxy, $C_1-C_4$ alkyl, phenyl, or $NR_{11}R_{12}$.

(bbb) Other preferred optional substitution is halo, hydroxy, acyl, $C_1-C_4$ alkoxy, $C_1-C_4$ alkyl, or phenyl.

(ccc) Preferred halo groups include bromine, chlorine, or fluorine.

(ddd) Other preferred halo groups include chlorine or fluorine.

(eee) Most preferred halo groups include fluorine.

(fff) Most preferred embodiments of the present invention are:

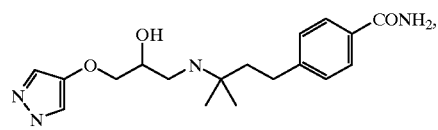

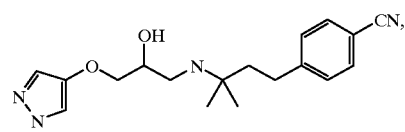

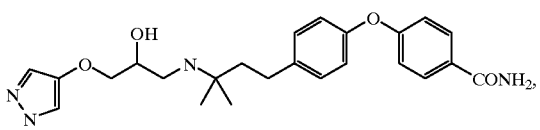

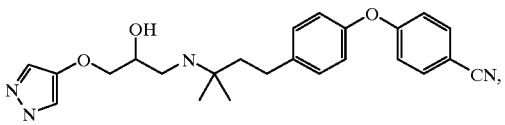

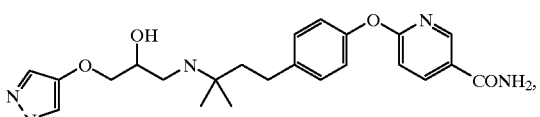

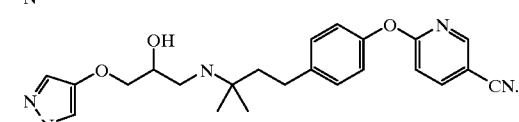

By virtue of their acidic moieties, some of the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include, but are not intended to be limited to, ammonium hydroxide, potassium carbonate, sodium bicarbonate, calcium hydroxide, methylamine, diethylamine, ethylenediamine, cyclohexylamine, ethanolamine, and the like.

Because of a basic moiety, some of the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include, but are not intended to be limited to, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, b-hydroxybutyrate, glycollate, maleate, tartrate, methanesulfonate, propanesulfonate, naphthalene-1-sulfonate, naphthalene-2-sulfonate, mandelate, and the like.

It is recognized that various stereoisomeric forms of the compounds of Formula I may exist. The compounds may be prepared as racemates and can be conveniently used as such. Alternatively, the compounds of the present invention can be prepared as single enatiomers or diastereomers by chiral synthesis or resolution techniques well known in the art. Therefore, the racemates, individual enantiomers, diastereomers, or mixtures thereof form part of the present invention. Unless otherwise specified, whenever a compound is described or referenced in this specification all the racemates, individual enantiomers, diastereomers, or mixtures thereof are included in said reference or description.

SYNTHESIS

The compounds of Formula I are prepared as described in the following Schemes and Examples. Schemes I and I describe methodology for the preparation of final embodiments of the present invention. Schemes III–VI represent methodology for the preparation of intermediates required for the construction of the final embodiments of the invention.

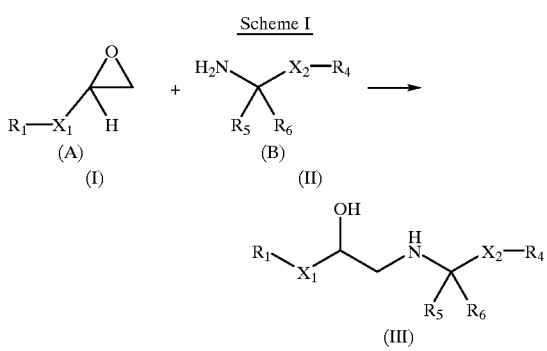

In Scheme I, $X_1$, $X_2$, $R_1$, $R_2$, $R_4$, $R_5$, and $R_6$ have the same meaning as previously described. The reaction of Scheme I is carried out under conditions known in the art for the amination of epoxides. For example, the epoxide (A) may be combined with the amine (B) in an alcohol, such as ethanol, at room temperature to the reflux temperature of the reaction mixture. Preferably, the reaction is carried under conditions generally described in Atkins et al., *Tetrahedron Lett.* 27:2451 (1986). These conditions include mixing the reagents in the presence of trimethylsilyl acetamide in a polar aprotic solvent such as acetonitrile, dimethylformamide (DMF), acetone, dimethylsulfoxide (DMSO), dioxane, diethylene glycol dimethyl ether (diglyme), tetrahydrofuran (THF), or other polar aprotic solvents in which the reagents are soluble. Preferably, the solvent is DMSO. The reaction is carried out at temperatures ranging from about 0° C. to about reflux.

Certain compounds of the present invention can be prepared by a combinatorial/parallel chemical array synthesis, as shown in Scheme II.

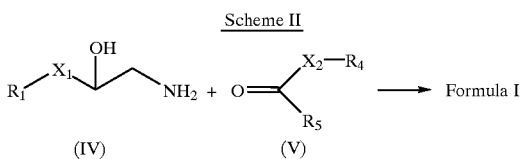

In Scheme II, $X_1$, $X_2$, $R_1$, $R_4$, and $R_5$ have the same meaning as previously described and $R_6$ is hydrogen. The reaction of Scheme II is preferably carried out by adding to a glass vial an amine (IV), ketone (V), and a non-reactive solvent such as methanol, DMF, methylene chloride, acetonitrile, or the like. The solution is shaken at room temperature to allow for imine formation and then treated with Amberlite IRA400 borohydride resin (Aldrich Chemicals). The slurry is then shaken for about 24 hours to effect reduction to the secondary amine. Methylene chloride and polystyrene-linked benzaldehyde resin (Frechet, J. M. et al., *J. Am Chem. Soc.* 93:492 (1971)) is added to the vial in order to scavenge excess primary amine starting material. The slurry is shaken, preferably overnight. The slurry is then filtered and the residual solids are rinsed with methanol. Evaporation under a flow of air, followed by drying for several hours at room temperature in a vacuum oven yields the desired product of sufficient purity.

A modification of Scheme II is necessary when the amine hydrochloride salt is used. Addition of resin-bound base to the initial reaction mixture prior to reduction or scavenging allows the desired reaction to proceed. Imine formation using amine hydrochloride salts, an aldehyde or ketone, and a resin bound amine base may be carried out using one of two different resins: poly(4-vinylpyridine) commercially available from Aldrich, and resin (VIII), which can be synthesized by the reaction of Merrifield resin with piperidine as is shown in Scheme IIa.

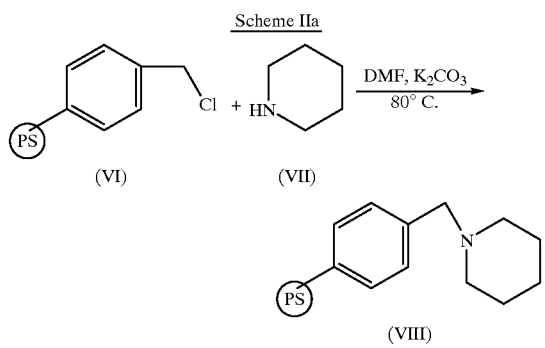

In Scheme IIa, PS is polysytrene. Both the poly(4-vinylpyridine) and resin (VIII) promote imine formation.

Scheme II can also be carried out by utilization of traditional techniques. For example, reductive aminations described in scheme II are well known in the art. They are typically performed by mixing the amine and ketone starting materials in a solvent and adding a reducing agent. Solvents typically include lower alcohols, DMF, and the like. Although a wide variety of reducing agents can be utilized, most commonly utilized are sodium borohydride, sodium cyanoborohydride, and the like. The reaction can be typically performed at room temperature to the reflux temperature of the solvent. Products can be isolated by techniques well known in the art.

The ketone and amino starting materials of Scheme II can be prepared by techniques which are well known by one skilled in the art. The synthesis of the starting materials is generally described in Schemes III and IV.

Scheme III

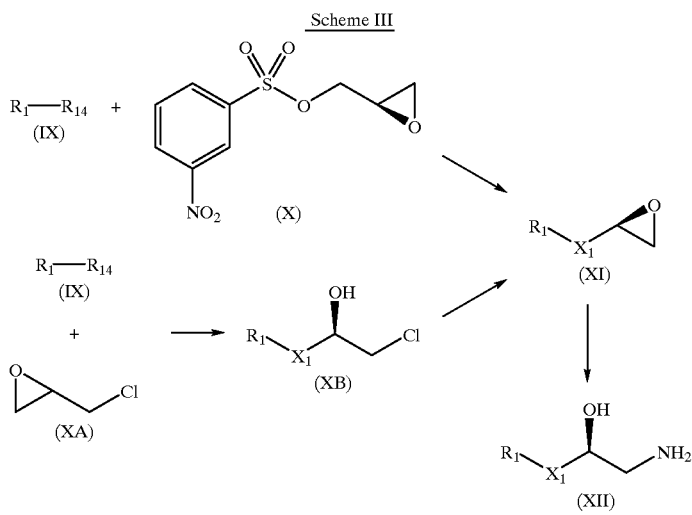

In Scheme III, $R_1$ is the same as previously defined. $R_{14}$ is OH or SH. Equimolar amounts of the aromatic compound (Compound IX) and (2S)-(+)-glycidyl 3-nitrobenzenesulfonate (Compound X) can be dissolved in an inert solvent such as acetone and treated with 1.1 equivalents of a non-reactive acid scavenger, such as $K_2CO_3$. The suspension is then heated at reflux for about 16–20 hours with stirring. The solvent can be removed in vacuo. The residue is partitioned between chloroform or other organic solvent and water. The organic layer can be dried over $Na_2SO_4$ and concentrated in vacuo to give the compound (XI) in sufficient purity (>95%) and yield (85–100%).

Alternatively, the compound of formula (IX) can be reacted with epichlorohydrin, by methods known in the art, to yield compounds of formula (XB). The compounds of formula (XB) can be closed to the epoxide compounds of formula (XI) by methods well known in the art.

The epoxide (XI) can be dissolved in an alcohol, preferably methanol, and treated with one equivalent of dibenzylamine. The solution is preferably stirred at reflux for about three to four hours and then cooled to ambient temperature. Approximately 10 equivalents of ammonium formate are added to the flask, followed by 10% palladium on carbon, and the suspension stirred vigorously at reflux for 30–45 minutes. The reaction mixture is cooled to room temperature and then filtered, concentrated in vacuo to a minimum volume and treated with 1.1 equivalents of a 1.0 M anhydrous solution of HCl in ether. The solution is concentrated to dryness. The solid residue is triturated with pentane to yield products of sufficient purity and yield. If desired, further purification may be carried out by passing over a short plug of silica, eluting with $CHCl_3$, then 95:5 $CHCl_3/$MeOH, then 25:5:1 $CHCl_3/MeOH/NH_4OH$.

Alternatively, the epoxide (XI) can be treated with a solution of methanol saturated with ammonia gas and stirred at room temperature in a sealed tube for 16 hours. This solution is then evaporated, and the residue subjected to standard purifications such as column chromatography or recrystallization. The HCl salt is then optionally produced by the addition of HCl gas in ether.

A skilled artisan would appreciate that, in order to increase yields or limit side products, it may be advantageous to appropriately protect the intermediates utilized in the synthesis of compounds of formula (XII). Choice of protecting groups will be governed by the ease of protection and deprotection as well as compatibility with the reaction conditions. A wide variety of protection strategies could be utilized to perform the transformations of scheme III. For examples see Greene T. W.; *Protective Groups in Organic Synthesis*, John Wiley and Sons, (1981).

The reaction of Scheme III is further described in U.S. Pat. No. 5,013,761 and references cited therein. U.S. Pat. No. 5,013,761 is herein incorporated by reference.

The ketone moieties of Scheme II, that are either unknown in the art or not commercially available, are prepared in accordance with Scheme IV.

Scheme IV

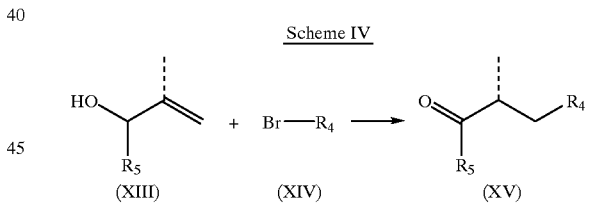

In Scheme IV, $R_4$ and $R_5$ are the same as previously defined. The notation ---- indicates optional branching. Preferably, $R_4$ is a substituted phenyl. The reaction described in Scheme IV is referred to as a Heck reaction and is described in A. J. Chalk et al., *J. Org. Chem.* 41: 1206 (1976). The reaction is achieved by treating compound (XIII) with an arylpalladium reagent. The arylpalladium reagent is generated in situ by treating Compound (XIV) with a palladium-triarylphosphine complex. The reaction is generally carried out in under conditions appreciated in the art.

Additional amines, of the type where $X_2$ is methylene, $R_4$ is aryl, and $R_{10}$ is aryl, heterocycle, optionally substituted aryl, or optionally substituted heterocycle, that are reacted in a manner analogous to Scheme I are prepared in accordance with Scheme V.

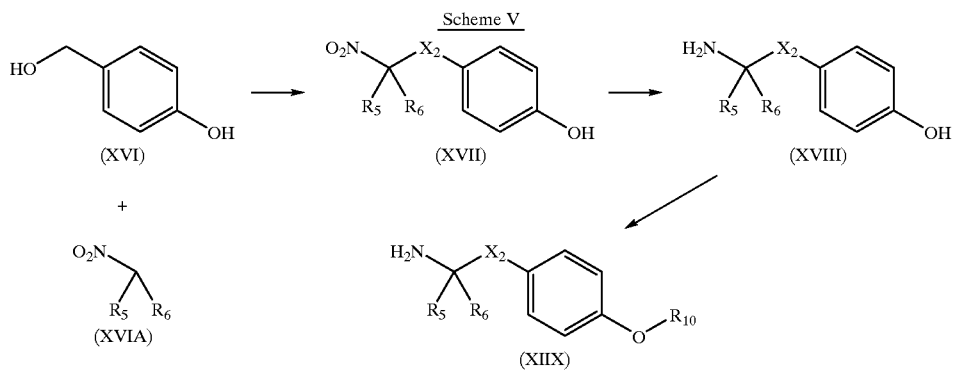

$R_5$, $R_6$, and $R_{10}$ are as previously defined and $X_2$ is methylene. (XVII) can be prepared by reacting 4-hydroxybenzyl alcohol with excess (about 5 mol/equiv) of a compound of formula (XVIA) by methods well known in the art (see Sh. Prikl. Kin., Vol 45, 1573–77 (1972); Russ.). The reaction can also be carried out by mixing the reagents in an aprotic solvent, preferably diglyme, and adding potassium t-butoxide (0.5 mol/equiv.). The reaction is then heated to reflux and water removed. After removal of water is complete, generally about 2–8 hours depending upon the scale of the reaction, the resulting solution is subjected to a standard aqueous work-up and the product is isolated by crystallization or other purification technique known in the art. Compound (XVII) can be reduced by methods well known in the art. Compound (XVIII) is preferably prepared by hydrogenation of the corresponding compound (XVII) over a precious metal catalyst. The hydrogenation can be affected at between about 20 and about 60 psi of hydrogen, and with a variety of solvents, temperatures, and catalysts well known in the art. The reaction is preferably carried out at about 50 psi of hydrogen over 5% palladium on carbon wetted with 2B3 ethanol. Compound (XVII) is charged to the reactor along with one equivalent of acetic acid, diluted with solvent, heated to about 50° C., and subjected to hydrogen for about 5–24 hours depending on the scale of the reaction. The product is isolated as the acetic acid salt upon work up by methods well known in the art.

A skilled artisan would appreciate that compound (XVIII) could be coupled with a wide variety of aromatic halides to yield the ethers contemplated by the present invention. The coupling can be carried out according to procedures well known in the art and is preferably performed by mixing the starting materials in N,N-dimethylacetamide and toluene in the presence of potassium carbonate. The reaction is then heated to reflux for about 5 to about 24 hours and water removed. The product is isolated by standard techniques. The crude product can be purified by methods well know in the art. A skilled artisan would appreciate that the amines prepared by Scheme V can be utilized in Scheme I to prepare compounds of the present invention.

Additional amines capable of being utilized in Scheme I can be prepared according to Scheme IV or by methods known in the art.

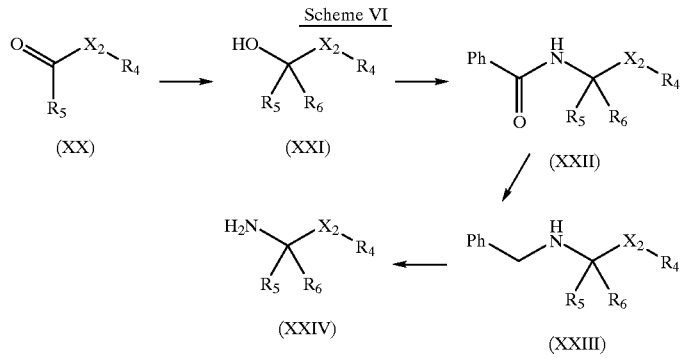

Compounds of formula XXI can be prepared by the addition of a nucleophile to the compounds of formula (XX) according to procedures well known in the art. The skilled artisan would appreciate a wide variety of conditions amenable to performing the additions. Preferred neucleophiles include, but are not intended to be limited to, alkyl grignard reagents, alkyl lithium reagents, and the like.

Compounds of formula (XXII) can be prepared from the compounds of formula (XXI) by the Ritter reaction. (See for example; *Organic Reactions*, Vol. 17,pp. 213–325, (1979)).

Compounds of formula (XXIII) can be prepared by reduction of the compounds of formula (XXII) according to procedures well known in the art. Preferred reducing agents include, but are not intended to be limited to, borane complexes and the like.

Compounds of formula (XXIV) can be prepared by reduction of the compounds of formula (XXIII) according to procedures well known in the art. (See for example; Greene T. W., *Protective Groups in Organic Synthesis*, John Wiley and Sons, (1981)).

Starting materials for the compounds described in Schemes I, II, III, IV or V are either commercially available, known in the art, or can be prepared by methods known in the art or described herein.

PREPARATIONS AND EXAMPLES

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography, gas chromatography, N,N-dimethylformamide, palladium on charcoal, tetrahydrofuran, ethyl acetate, thin layer chromatography and elemental analysis are abbreviated M.Pt., NMR, MS, HPLC, GC, DMF, Pd/C, THF, EtOAc, TLC, and EA respectively. The terms "EA", "TLC", "NMR", and "MS", when utilized in the preparations, indicate that the data indicated was consistent with the desired structure.

Preparations 1 through 14 describe syntheses of compounds utilized in combinatorial chemical synthesis of scheme II.

Preparation 1

4-(3-Oxobutyl)-1-(2-oxazolidine)benzene

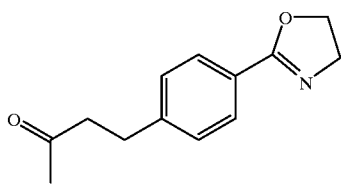

4-Bromo-1-(2-oxazolidine)benzene (3.0 g, 13.3 mmol), 3-buten-2-ol (1.4 g, 20 mmol), Pd(OAc)$_2$ (60 mg, 0.26 mmol), (o-tolyl)$_3$P (158 mg, 0.52 mmol), sodium bicarbonate (1.34 g, 15.9 mmol) in 30 mL of N-methylpyrrolidinone was heated under nitrogen at 130° C. for 1 hour. The reaction mixture was then cooled and partitioned between ethyl acetate and water. The combined organic layers were washed with water and then dried (Na$_2$SO$_4$), filtered, and concentrated in vacuo to yield 2.6 g of a tan oil. Purification by flash chromatography (silica gel, 1:1 ethyl acetate/hexane) yielded 1.9 g of a pale yellow oil which crystallized upon drying under vacuum. Recrystallization from hexane gave 1.47 g (49%) of white needles, m.p. 62–64° C. NMR. MS.

Preparation 2

4-[4-(3-Oxobutyl)phenoxy]benzonitrile

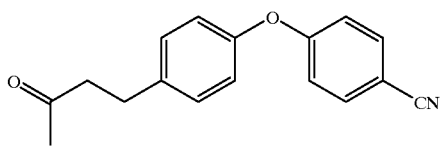

4-Fluorobenzonitrile (6.05 g, 50 mmol), 4-(4-hydroxyphenyl)-2-butanone (8.21 g, 50 mmol) and potassium carbonate (8.3 g, 60 mmol) were dissolved in N,N-dimethylacetamide (50 mL) and heated at 150° C. for 4 hours under nitrogen. The reaction mixture was then poured into 800 mL of ice water. A slowly crystallizing solid was filtered to give 13 g of crude product. This material was recrystallized from ethanol/water (3:1) to give 10.48 g (79%) of pale brown crystals, m.p. 64–66° C. EA. NMR. MS.

Preparation 3

[4-(3-Oxobutyl)phenoxy]benzamide

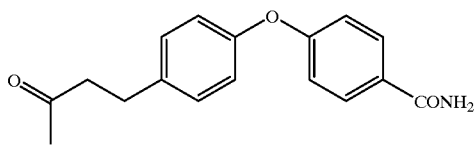

4-[4-(3-Oxobutyl)phenoxy]benzonitrile (6.0 g, 22.6 mmol) and potassium carbonate (1.0 g, 7.2 mmol) were slurried in DMSO (50 mL) and cooled to 0° C. in an ice bath. Aqueous 30% hydrogen peroxide (6 mL) was added slowly, and the mixture stirred at 0° C. for 1 hour. The reaction was quenched by pouring into 500 mL water, and the subsequent white precipitate was collected and washed with water. This material was recrystallized from 300 mL ethanol to give 5.35 g (84%) white crystals, m.p. 169–172° C. NMR. MS. EA.

Preparation 4

2-Triphenylmethyl-5-chloromethyltetrazole

5-Chloromethyltetrazole (1.19 g, 10 mmol) in CH$_2$Cl$_2$ (10 mL) was treated with triphenylmethyl chloride (2.79 g, 10 mmol) and diisopropylethylamine (2.0 mL, 11.5 mmol) and stirred for 40 minutes at room temperature. The reaction mixture was concentrated in vacuo and partitioned between ethyl acetate/water. The organic layer was washed with saturated NaHCO$_3$ solution, then brine, dried (Na$_2$SO$_4$) and concentrated in vacuo to yield 3.48 g of an off-white solid. Trituration of this residue in diethyl ether yielded 3.04 g (84%) of a white solid, m.p. 162–165° C. NMR. MS. EA.

Preparation 5

5-[4-(2-Oxobutyl)phenoxymethyl]tetrazole

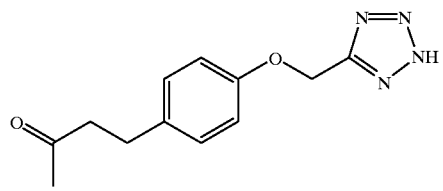

4-(4-Hydroxyphenyl)-2-butanone (493 mg, 3 mmol) was cooled to 5° C. and treated with NaH (180 mg, 4.5 mmol, 60% in mineral oil) under nitrogen. After 15 minutes the ice bath was removed and the solution allowed to warm to room temperature over 45 minutes. The reaction was cooled to 5° C. and treated with 2-triphenylmethyl-5-chloromethyltetrazole (1.08 g, 3 mmol) and stirred at room temperature for 3 hours. The reaction mixture was poured into EtOAc (300 mL), and washed with water then brine. The organic layer was dried (MgSO$_4$) and concentrated in vacuo to provide a yellow solid. This material was suspended in a mixture of MeOH (100 mL) and THF (50 mL) and treated with 4N HCl in dioxane (7.5 mL, 30 mmol). The resulting mixture was stirred for 1.5 hr. and then concentrated in vacuo to provide a tan solid. The residue was applied to a silica chromatography column and eluted with 33–100% ethyl acetate in hexane to provide 235 mg (32%) of a white solid, m.p. 148–150° C. NMR. MS. EA.

Preparation 6

3-[4-(2-Oxobutyl)phenoxymethyl]pyridine

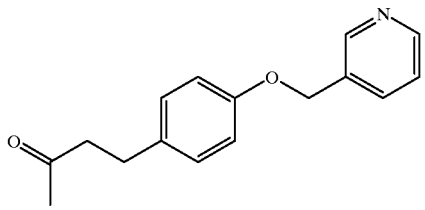

4-(4-Hydroxyphenyl)-2-butanone (4.11 g, 25 mmol) and potassium carbonate (10.37 g, 75 mmol) in acetone (30 mL) was treated with 3-picolyl chloride hydrochloride (4.27 g, 26 mmol) under nitrogen. The mixture was stirred at reflux for 21 hours, proceeding about 50% towards completion. Potassium iodide (2.0 g, 13 mmol, 0.5 eq) was added and after 3 hours no picolyl chloride was observed on TLC. The volatiles were removed in vacuo and the resulting residue partitioned between EtOAc/water. The combined organic layers were washed with water, saturated NaHCO$_3$ solution, 10% Na$_2$SO$_3$, and then brine. The organic layer was dried (MgSO$_4$) and concentrated in vacuo to provide 4.8 g of a yellow oil. The material was purified on a Waters Prep 2000LC by elution with 10–80% ethyl acetate in hexanes over 45 minutes to yield 2.20 g (34%) of an oil which solidified on standing, m.p. 35–37° C. NMR. MS. EA.

Preparation 7

2,6-Dimethoxy-4-[4-(2-oxobutyl)phenoxy]-1,3,5-triazine

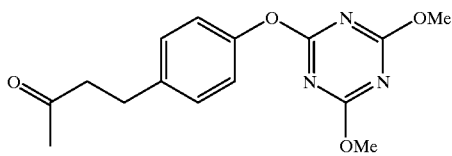

4-(4-Hydroxyphenyl)-2-butanone (4.93 g, 30 mmol) was added to a solution of sodium methoxide (1.62 g, 30 mmol) in methanol (150 mL) under nitrogen. After stirring for 1 hour the methanol was removed in vacuo and the residue suspended in acetone (200 mL). The suspension was treated with 4,6-dimethoxy-2-chlorotriazine and refluxed for 3 hours. The volatiles were removed in vacuo and the residue partitioned between ethyl acetate/water. The organic layers were dried (MgSO$_4$) and concentrated in vacuo to provide 10.28 g of a white semi-solid. The material was purified on a Waters Prep 2000LC by elution with a gradient of 20–60% ethyl acetate in hexanes over 55 minutes to yield 4.43 g (49%) of a colorless oil. NMR. MS. EA.

Preparation 8

2-[4-(2-Oxobutyl)phenoxy]-5-carboxamidopyridine

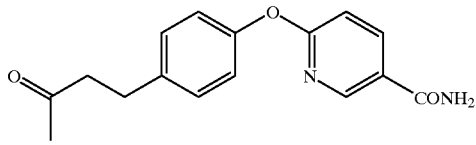

4-(4-Hydroxyphenyl)-2-butanone (3.28 g, 20 mmol) in anhydrous DMF (150 mL) was treated with NaH (1.2 g, 30 mmol, 60% in mineral oil) under nitrogen. The solution was stirred for 30 minutes at ambient temperature and then treated with 6-chloronicotinamide (3.13 g, 20 mmol). The reaction was stirred at 60° C. for 1.5 hours and then 90° C. for five hours. The reaction was allowed to cool, poured into 50% saturated ammonium chloride solution, and extracted with EtOAc. The organic layer was dried (MgSO$_4$) and concentrated in vacuo with a xylene azeotrope to yield 11.4 g of a brown oil. The material was purified on a Waters Prep 2000LC by elution with 75–100% EtOAc over 60 minutes. The resulting material was triturated in cold EtOAc and collected by filtration to provide 2.73 g (48%) white solid m.p. 137–139° C. EA. NMR. MS.

Preparation 9

2-[4-(2-Oxopropyl)phenoxy]-5-carboxamidopyridine

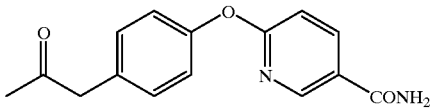

In a manner similar to the above examples, 3-(4-hydroxyphenyl)-2-propanone (2.25 g, 15 mmol) was treated with NaH (0.9 g, 22.5 mmol, 60% in mineral oil) followed by reaction with 6-chloronicotinamide (2.34 g, 15 mmol). Following work-up the material was purified on a Waters Prep 2000LC to provide 1.28 g (32%) of a light yellow solid. m.p. 172–174° C. NMR. MS. EA.

Preparation 10

{4-[(2-Oxocyclohexyl)methyl]benzonitrile

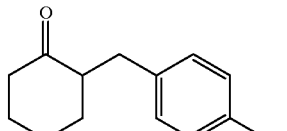

A mixture of methyl cyclohexanone-2-carboxylate (11.0 g, 70 mmol, from Fluka), a-bromo-p-tolunitrile (12.3 g, 63 mmol), potassium carbonate (10.5 g, 76 mmol) in THF (200 mL) was refluxed for 24 hours. The progress of the reaction was followed by GC. The reaction was diluted with water and the THF was removed under reduced pressure. The aqueous portion was extracted with EtOAc, dried (MgSO$_4$) to give 19.3 g of a white solid that was 74% pure by gas chromatrophy. The solid was recrystallized from hexane/EtOAc to give 7.75 g white crystals that were 100% pure by glc. A second crop of 3.65 g was obtained by adding more hexane to the filtrate. Overall, 11.4 g (67%) of 1-[(4-cyanophenyl)methyl]-1-methoxycarbonyl-2-oxocyclohexane carboxylate, was obtained; mp 82–84° C. NMR. MS.

Under a blanket of nitrogen, a mixture of 1-[(4-cyanophenyl)methyl]-1-methoxycarbonyl-2-oxocyclohexane carboxylate (7.6 g, 28 mmol), sodium cyanide (2.1 g, 42 mmol) and DMSO (100 mL) was heated at 115° C. for 1.5 hours. The progress of the reaction was monitored by glc. The reaction was cooled and partitioned between water, EtOAc and brine. The organic layer was washed with water and dried ($MgSO_4$). After concentration, crude product was obtained as a tan oil. Purification by plug filtration (200 g silica gel, 15% EtOAc/hexane) gave 3.3 g (55%) product as colorless oil. NMR. MS.

Preparation 11

[(2-Oxocyclohexyl)methyl]benzamide

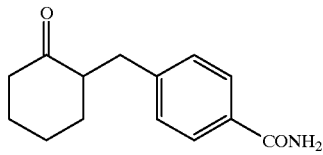

A DMSO (20 mL) solution of the compound of Preparation 28 (2.5 g, 11.7 mmol) was cooled in an ice bath. Solid $K_2CO_3$ (500 mg) was added followed immediately by 30% $H_2O_2$ (3 mL). After 20 minutes, TLC (3/7 EtOAc/hexane) showed a trace of starting material remained. The ice bath was removed and the reaction was stirred and room temperature for 1 hour. The reaction was diluted with 500 mL water and the white solid collected and dried to give 2.44 g (90%) desired amide. The product was recrystallized from 1/9 EtOAc/hexane to give 2.02 g of the titled product as white crystals, mp 167–170° C. NMR. MS.

Preparation 12

Tetralone-6-carboxylic acid, ethylene ketal

6-Bromo-2-tetralone (2.0 g, 8.89 mmol) was dissolved in toluene (50 mL) and treated with excess ethylene glycol (4.88 mL, 88.9 mmol) and catalytic p-toluenesulfonic acid (15 mg). The solution was stirred at reflux 16 hours, and water was removed from the reaction mixture using a Dean-Stark condenser. After cooling to ambient temperature, the toluene solution was washed 2×1N NaOH, 1×water, 1×brine, dried over $Na_2SO_4$ and concentrated in vacuo to give 2.23 g (93%) of 6-bromo-2-tetralone ethylene ketal as a brown oil which was used without further purification.

6-Bromo-2-tetralone ethylene ketal (2.2 g, 8.15 mmol) was dissolved in anhydrous THF (30 mL), cooled to −78° C. and treated with tert-butyllithium (12.05 mL, 20.4 mmol, 1.7M in pentane) under an atmosphere of nitrogen. After stirring for 30 minutes, anhydrous carbon dioxide gas was passed through the reaction mixture for 20 minutes at −78° C. The suspension was then allowed to warm to ambient temperature. The solution was quenched with water and acidified with 1N HCl, then extracted 2×EtOAc. The organic extracts were washed with brine, dried over $Na_2SO_4$ and concentrated in vacuo to a pale brown oil. The oily residue was applied to a silica flash chromatography column and eluted with 30%–50% EtOAC in hexanes to yield Tetralone-6-carboxylic acid, ethylene ketal 1.06 g (55%) of a slowly crystallizing solid. NMR. MS.

Preparation 13

Tetralone-6-carboxamide

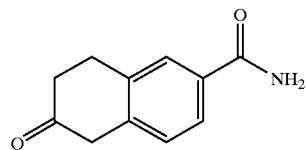

Tetralone-6-carboxylic acid, ethylene ketal (395 mg, 2.07 mmol) was codissolved in $CH_2Cl_2$ (50 mL) with N-hydroxysuccinimide (260 mg, 2.76 mmol) at 0° C. and treated with a slight excess of 1,3-dicyclohexylcarbodiimide (502 mg, 2.50 mmol). The mixture was allowed to warm to ambient temperature over 30 minutes, during which time a fine white precipitate formed. Ammonium chloride (333 mg, 6.23 mmol) and triethylamine (1.58 mL, 12.5 mmol, d=0.797) were added. The solution was stirred at ambient temperature for 16 hours. The suspended urea and salts were filtered away and the solution concentrated in vacuo to a colorless oil. The oil was applied to a silica flash chromatography column and eluted with 50–100% EtOAc in hexanes to yield 250 mg (64%) of 2-tetralone-6-carboxamide, ethylene ketal as a white solid, clean by NMR, TLC.

2-Tetralone-6-carboxamide ethylene ketal (250 mg, 1.07 mmol) and catalytic p-toluenesulfonic acid were stirred in acetone (50 mL) at ambient temperature for 48 hours. The volatiles were removed in vacuo and the residue triturated in ethyl acetate. The solids were filtered, washed and dried to yield 77.5 mg (38%) of 2-Tetralone-6-carboxamide as a white powder, pure by NMR, TLC. MS.

Preparation 14

Tetralone-6-morpholinamide

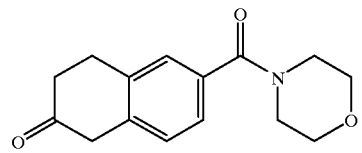

2-Tetralone-6-carboxylic acid, ethylene ketal (395 mg, 2.07 mmol) was co-dissolved in $CH_2Cl_2$ (50 mL) with N-hydroxysuccinimide (260 mg, 2.76 mmol) at 0° C. and treated with a slight excess of 1,3-dicyclohexylcarbodiimide (502 mg, 2.50 mmol). The mixture was allowed to warm to ambient temperature over 30 minutes, during which time a fine white precipitate formed. Morpholine (0.91 mL, 10.4 mmol, d=0.998) was added and the solution stirred at ambient temperature for 16 hours. The suspended urea was filtered away and the solution concentrated in vacuo to a colorless oil. The oil was applied to a silica flash chromatography column and eluted with 50–100% EtOAc in hexanes to yield 323 mg (51%) of 2-tetralone-6-morpholinamide, ethylene ketal as a slowly crystallizing solid, clean by NMR, TLC.

2-Tetralone-6-morpholinamide, ethylene ketal (323 mg, 1.06 mmol) and catalytic p-toluenesulfonic acid were stirred in acetone (50 mL) at ambient temperature for 48 hours. TLC indicated a mixture of 2-tetralone-6-morpholinamide, ethylene ketal and desired product, so the solution was heated to reflux for 16 hours. The volatiles were removed in vacuo and the residue applied to a silica flash chromatography column and eluted with 50–100% EtOAc in hexanes to yield 27 mg (10%) of 2-tetralone-6-morpholinamide a slowly crystallizing solid, pure by NMR, TLC. MS.

The following compounds were prepared in a manner analogous to schemes IV and/or preparations 1 through 14 described herein or by techniques appreciated in the art. All compounds were confirmed by NMR and MS with the exception that preparation 66 was confirmed by only NMR.

| Name | Structure | m.p. | Yield |
| --- | --- | --- | --- |
| 4-(3-oxobutyl)benzonitrile<br>Preparation 15 | 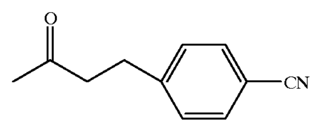 | oil | 33% |
| 3-(3-oxobutyl)benzonitrile<br>Preparation 16 | 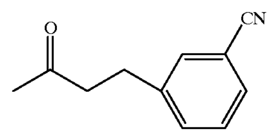 | oil | 44% |
| 3-(3-oxobutyl)benzamide<br>Preparation 17 | 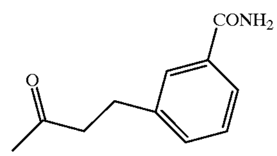 | 104–6 | 45% |
| 2-(3-oxobutyl)benzonitrile<br>Preparation 18 | 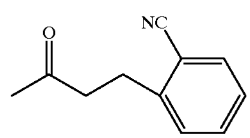 | oil | 43% |
| (2-(3-oxobutyl)benzamide<br>Preparation 19 | 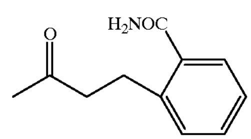 | 113–114 | 91% |
| 4-(3-oxohexyl)benzonitrile<br>Preparation 20 | 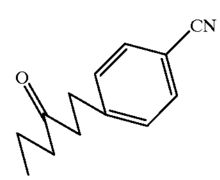 | oil | 85% |
| 4-(3-oxohexyl)benzamide<br>Preparation 21 | 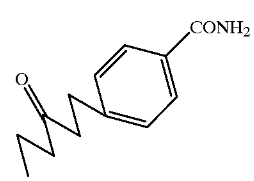 | 90–93 | 67% |

-continued

| Name | Structure | m.p. | Yield |
|---|---|---|---|
| 3-methyl-5-(4-(3-oxobutyl)phenyl)-1H-tetrazole<br>Preparation 22 | 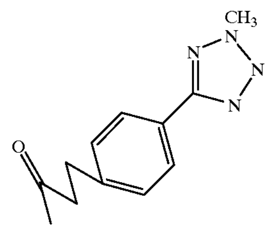 | 90–93 | 67% |
| (4-(3-oxobutyl)phenyl)sulfonamide<br>Preparation 23 | 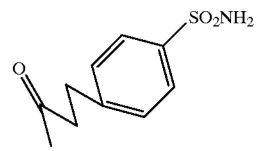 | 132–4 | 36% |
| 4-(1-methyl-3-oxobutyl)benzonitrile<br>Preparation 24 | 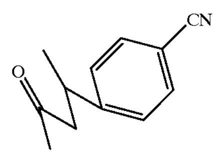 | oil | 44% |
| 3-benzyl-5-(4-(3-oxobutyl)phenyl)-1H-tetrazole<br>Preparation 25 | 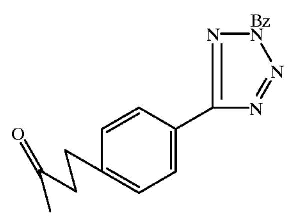 | 66–9 | 41% |
| 4-(1-methyl-3-oxobutyl)benzamide<br>Preparation 26 | 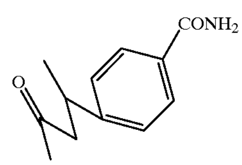 | 127–9 | 95% |
| 5-(4-(3-oxobutenyl)phenyl)-1H-tetrazole<br>Preparation 27 | 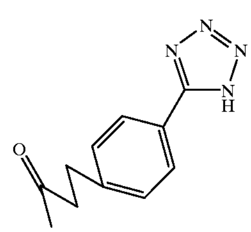 | 197–9 | 94% |
| 5-(3-oxobutyl)-2-furanoic acid<br>Preparation 28 | 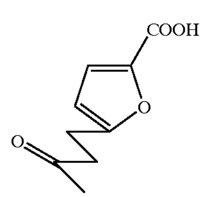 | 129–32 | 86% |

-continued

| Name | Structure | m.p. | Yield |
|---|---|---|---|
| 3-(2-fluoro-4-(3-oxobutyl)phenyl) propenoic acid Preparation 29 | 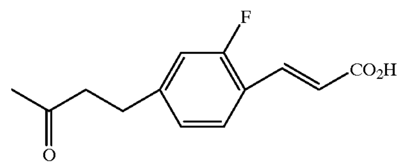 | 143–6 | 95% |
| 4-(3-oxobutyl)-1-cyanomethylbenzene Preparation 30 | 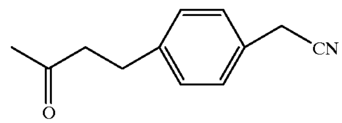 | oil | 100% |
| (4-(3-oxobutyl)phenyl)thioamide Preparation 31 | 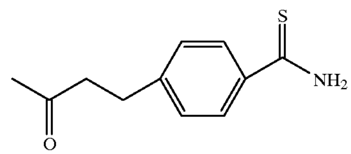 | 96–8 | low* |
| (2-fluoro-4-(3-oxobutyl)benzonitrile Preparation 32 | 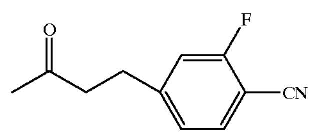 | oil | 78% |
| 2-fluoro-4-(3-oxobutyl)benzamide Preparation 33 | 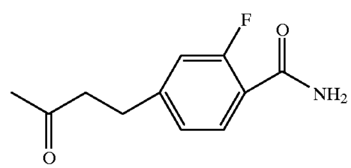 | 150–3 | 85% |
| 3-methyl-5-(2-(3-oxobutyl)phenyl-1N-tetrazole Preparation 34 | 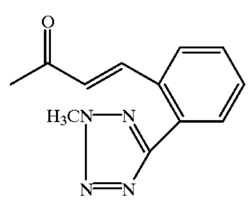 | 64–5 | 45% |
| 4-(3-oxocyclohexyl)benzonitrile Preparation 35 | 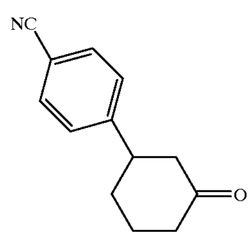 | 66–69 | 36% |
| 1-methyl-5-(2-(3-oxobutenyl)phenyl)-1H-tetrazole Preparation 36 | 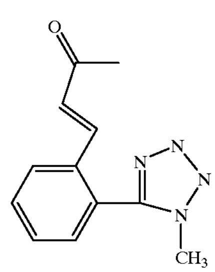 | 100–102 | 18% |

-continued

| Name | Structure | m.p. | Yield |
|---|---|---|---|
| (2,6-difluoro-(4-(3-oxobutyl)phenyl))sulfonamide<br>Preparation 37 | | oil | 41% |
| N-methoxyl-4-(3-oxobutyl)benzamide<br>Preparation 38 | | | low |
| 4-(2-methyl-3-oxobutyl)benzonitrile<br>Preparation 39 | | oil | 66% |
| 4-(2-methyl-3-oxobutyl)benzamide<br>Preparation 40 | | 112–115 | 87% |
| (1-methyl-2-(4-(3-oxobutyl)phenyl)-4-trifluoromethyl)imidazole<br>Preparation 41 | | 62–3 | 68% |
| 4-(1,2-dimethyl-3-oxobutyl)benzamide<br>Preparation 42 | | 100–102 | 90% |
| 4-(3-oxocyclohexyl)benzamide<br>Preparation 43 | | 188–91 | 42% |
| 5-(3-oxobutyl)-2-thiophene sulfonamide<br>Preparation 44 | | 96–98 | 66% |
| (3-(3-oxobutyl)phenyl)sulfonamide<br>Preparation 45 | | 87–90 | 35% |

-continued

| Name | Structure | m.p. | Yield |
|---|---|---|---|
| 2-methyl-5-(3-(3-oxobutyl)phenoxy) phenyl)tetrazole Preparation 46 | 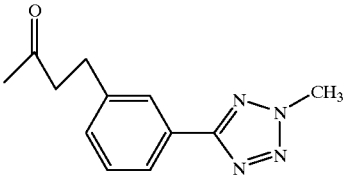 | 98 | 65% |
| 4-(3-oxocyclopentyl)benzamide Preparation 47 | 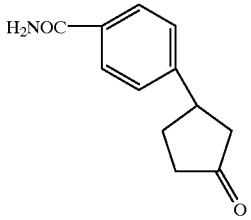 | 203–4 | 43% |
| 4-(1,1-dimethyl-3-oxobutyl)benzamide Preparation 48 | 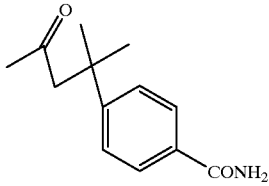 | 106–8 | 61% |
| 4-(3-oxocycloheptyl)benzonitrile Preparation 49 | 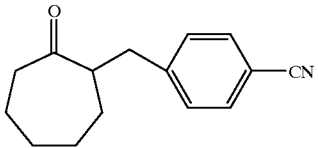 | oil | 54% |
| 4-(3-oxohexyl)benzonitrile Preparation 50 | 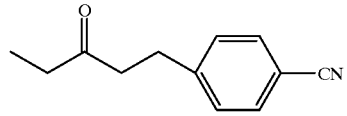 | oil | 77% |
| 4-(3-oxobutyl)phthalhydrazide Preparation 51 | 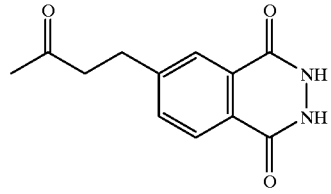 | 161–4 | 13% |
| 4-(3-oxohexyl)benzamide Preparation 52 | 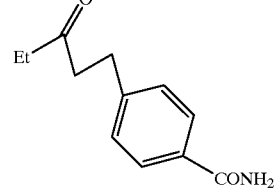 | 158–61 | 82% |
| 4-(2,2-dimethyl-3-oxobutyl)benzonitrile Preparation 53 | 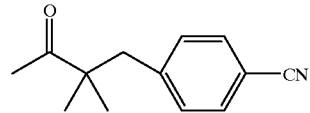 | oil | 72% |

-continued

| Name | Structure | m.p. | Yield |
|---|---|---|---|
| 4-(2,2-dimethyl-3-oxobutyl)benzamide Preparation 54 | 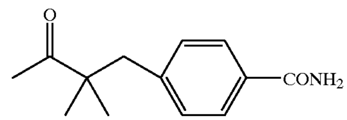 | 127–131 | 62% |
| 5-(2-methyl-3-oxobutyl)-2-thiophene sulfonamide Preparation 55 | 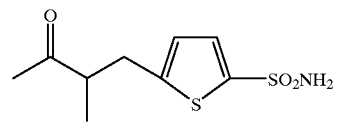 | oil | low |
| 4-((2-oxocycloheptyl)methyl)benzamide Preparation 56 | 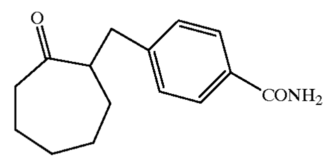 | 132–4 | 88% |
| 4-((2-oxocyclopentyl)benzonitrile Preparation 57 | 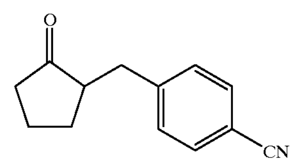 | oil | 62% |
| 4-((2-oxocyclopentyl)methyl)benzamide Preparation 58 | 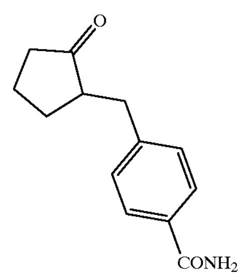 | 138–142 | 81% |
| 4-(4-(3-oxobutyl)phenoxy)benzonitrile Preparation 59 | 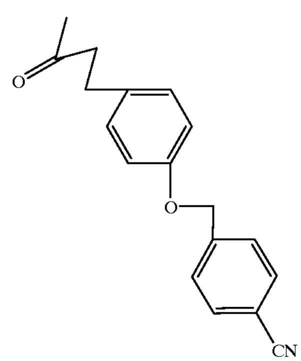 | 94–7 | 84% |

-continued

| Name | Structure | m.p. | Yield |
|---|---|---|---|
| 4-(4-(3-oxobutyl)phenoxy)methyl benzamide Preparation 60 | | 215–17 | 95% |
| 2-fluoro-4-(2-methyl-3-oxobutyl)benzonitrile Preparation 61 | | oil | 42% |
| 2-fluoro-4-(2-methyl-3-oxobutyl)benzamide Preparation 62 | | 112–15 | 93% |
| 5-(2-fluoro-4-(2-methyl-3-oxobutyl) phenyl)-1H-tetrazole Preparation 63 | | 175–8 | 32% |
| 5-(3-oxobutyl)-2-(morpholinosulfonyl)- thiophene Preparation 64 | | 80–83 | 69% |
| 5-(2-methyl-3-oxobutyl)-2-(morpholinosulfonyl)- thiophene Preparation 65 | | oil | 15% |
| 4-(2-(4-(3-oxobutyl)phenoxy)ethyl) benzonitrile Preparation 66 | | oil | 41% |

-continued

| Name | Structure | m.p. | Yield |
|---|---|---|---|
| 4-(4-(3-oxobutyl)phenyl)benzonitrile Preparation 67 | 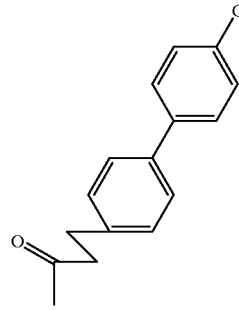 | 133–5 | 62% |
| 2-methyl-4-(3-oxobutyl)benzonitrile Preparation 68 | 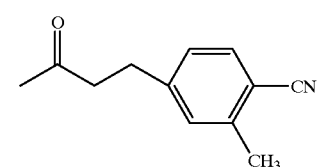 | oil | 55% |
| 4-(4-(3-oxobutyl)phenyl)benzamide Preparation 69 | 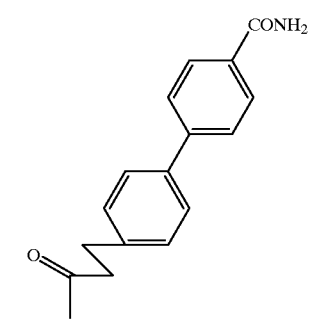 | 229–31 | 94% |
| (3-methyl-4-(3-oxobutyl)phenyl) methanenitrile Preparation 70 | 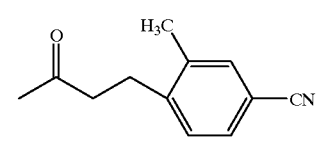 | 34–6 | 75% |
| 2-methyl-4-(3-oxobutyl)benzamide Preparation 71 | 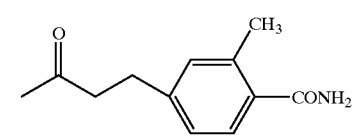 | 147–50 | 39% |
| 3-methyl-4-(3-oxobutyl)benzamide Preparation 72 | 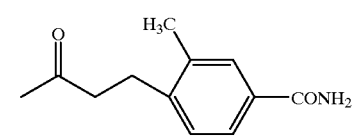 | 103–5 | 46% |
| 4-(2-(4-(3-oxobutyl)phenoxy)ethyl)benzamide Preparation 73 |  | semi-solid | 17% |
| 4-(4-oxopentyl)benzonitrile Preparation 74 | 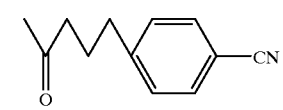 | oil | quant |

-continued

| Name | Structure | m.p. | Yield |
|---|---|---|---|
| 4-(4-oxopentyl)benzamide Preparation 75 | 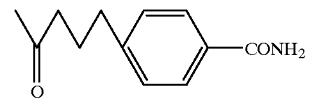 | 111–13 | 87% |
| 3-methyl-4-(2-methyl-3-oxobutyl)benzonitrile Preparation 76 | 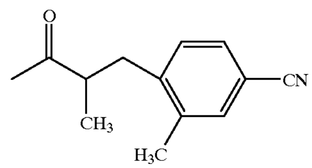 | oil | 64% |
| (3-methyl-4-(2-methyl-3-oxobutyl)benzamide Preparation 77 | 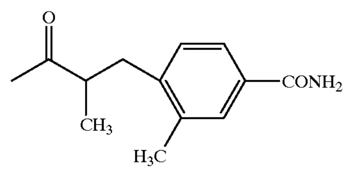 | 105–7 | 71% |
| 4-(2,5-dimethyl-4-(3-oxobutyl)phenoxy) benzonitrile Preparation 78 | 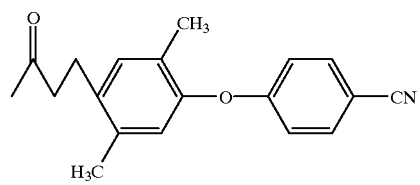 | 57–9 | low |
| 4-(2-ethyl-3-oxobutyl)benzoic acid Preparation 79 | 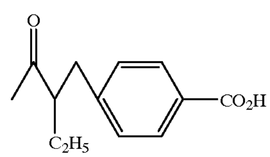 | 126–9 | 24% |
| 4-(2,5-dimethyl-(3-oxobutyl)phenoxy)benzamide Preparation 80 | 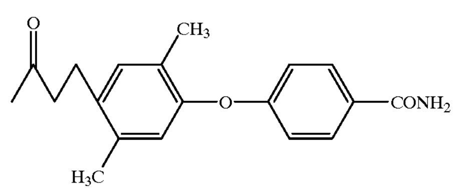 | 191–3 | 76% |
| (4-2,6-dimethyl-(3-oxobutyl)phenoxy) phenyl)methanenitrile Preparation 81 | 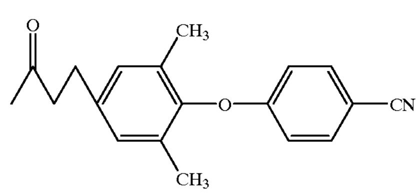 | yellow oil | 72% |
| 4-(2,6-dimethyl-(3-oxobutyl)phenoxy)benzamide Preparation 82 | 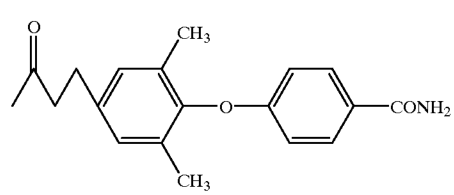 | 238–41 | 63% |

Preparation 83

4-(2-Methyl-2-nitropropyl)phenol

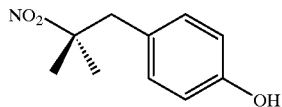

A mixture of 4-hydroxybenzyl alcohol (100.08 g, 806 mmol), 2-nitropropane (400 mL, 4.45 mol) and diglyme (800 mL) was heated to 38° C. Potassium t-butoxide (45.29 g, 403.6 mmol) was added, and the mixture was heated to reflux at 132° C. with a Dean-Stark trap. Water began collecting in the trap, and continued at a high rate for approximately 1.5 h. When water collection slowed (around 2.5 h) then aliquats of solvent (30–40 mL each) were removed every thirty minutes. During the water collection and solvent removal the temperature rose from 132° C. to 149° C. After 4 h less than 1% of the 4-hydroxybenzyl alcohol remained by HPLC analysis. The heating mantle was removed, and the reaction mixture was allowed to cool. When the temperature was 100° C. water (200 mL) was added, and the solution was allowed to cool to room temperature. Solvent was removed on a rotary evaporator under vacuum until 593 g of solution remained. Water (500 mL) and EtOAc (500 mL) were added and the layers were separated, and the aqueous layer was extracted with EtOAc (200 mL), and the combined organic layers were extracted with 1N HCl (500 mL) and water (300 mL). The organic layer was distilled in vacuo to 261 g of oil to which EtOAc was added (160 mL). Heptane (3.4 L) was added rapidly with vigorous stirring for 30 min, and the product crystallized to yield a beige solid (112.36 g, 71% yield, >98% purity by HPLC analysis). Another crop of crystals may be obtained from the filtrate by concentrating and filtering the solids, or by concentrating more fully to a solution and adding heptane to crystallize. NMR, MS, and EA.

Preparation 84

4-(2-Amino-2-methylpropyl)phenol acetic acid salt

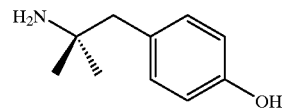

A one-gallon high-pressure reactor was charged with 4(2-methyl-2-nitropropyl)phenol (120 g, 614 mmol), HOAc (35.2 mL, 614 mmol), 5% Palladium on carbon (24 g) wetted with 2B3 EtOH (60 mL), and MeOH (1230 mL). The mixture was heated to 50° C. with agitation (600 rpm), and the reactor was purged with $N_2$ and pressurized to 50 psi with $H_2$. After 15.5 h the reactor was purged with $N_2$, and the cooled mixture was filtered. The filter cake was washed with MeOH and the filtrate was concentrated to 514 g of slurry on a rotary evaporator. To this slurry was added EtOAc (2 L) with vigorous agitation. After stirring for 1 h, the resulting crystals were filtered and washed with a small amount of EtOAc. The product was dried overnight in a 45° C. vacuum oven to yield 118.83 g (86%) of product as small white needles (mp 211–216° C. dec). This material was 99% pure by HPLC analysis, and while another 9.00 g of material was obtained from the mother liquor it was found to be only 88% pure. NMR. EA.

Preparation 85

2-(4-(2-Amino-2-methylpropyl)phenoxy)-5-carboxamidepyridine

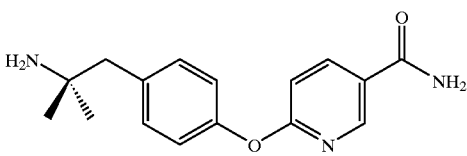

A mixture of 4-(2-amino-2-methylpropyl)phenol acetic acid salt (45.06 g, 200 mmol), powdered $K_2CO_3$ (69.1 g, 500 mmol), 6-chloronicotinamide (31.32 g, 200 mmol), DMAC (622 mL) and iso-octane (70 mL) was slowly heated to reflux at 140° C. A water trap filled with iso-octane was used to collect water formed in the reaction, and reflux was maintained for 5.5 h. The mixture was allowed to cool to room temperature, and the solids were filtered and washed with EtOAc. The filtrate was concentrated in vacuo to 88.6 g of solid which was dissolved in EtOAc (500 mL). To this solution was added water (800 mL), 1N HCl (200 mL) and MeOH (50 mL). The pH of this mixture was adjusted to 7.2 with con. HCl, and the aqueous layer was separated and washed with methyl t-butyl ether (500 mL). The product was crystallized by addition of 10N NaOH (20 mL) which raised the pH to 11.This pH was maintained by addition of 10N NaOH as needed during the course of the crystallization (90 min). The product was filtered, washed with water and dried in vacuo at 45° C. to 53.11 g (93%) of white solid which was >98% pure by HPLC analysis: $^1$H NMR (300 MHz, DMSO-$d_6$) NMR was consistent with the desired product.

Preparation 86

4-(4-(2-Amino-2-methylpropyl)phenoxy)benzonitrile

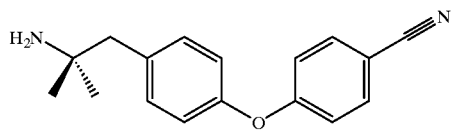

A mixture of 4-(2-amino-2-methylpropyl)phenol acetic acid salt (45.06 g, 200 mmol), powdered $K_2CO_3$ (69.1 g, 500 mmol), and DMAC (550 mL) was heated to 75–100° C. Toluene (166 mL) was added, and the mixture was slowly heated to reflux at 134° C. The reflux temperature was raised by distillation of toluene and water into a water trap until the temperature reached 141° C. The mixture was then allowed to cool to below 100° C. at which point 4-fluorobenzonitrile (24.46 g, 202 mmol) was added along with 50 mL of toluene. The mixture was again heated to reflux at 140° C. with water being collected in a toluene-filled water trap for 4 h. The mixture was allowed to cool to room temperature, and the solids were filtered and rinsed with toluene. The filtrate was concentrated on a rotary evaporator to 77 g of syrup which was dissolved in EtOAc (400 mL). This solution was extracted with water (400 mL), and the aqueous layer was back-extracted with EtOAc (100 mL). The combined organic layers were washed with water (3×400 mL) and concentrated in vacuo to 53.4 g (100%) of oil which was >98% pure by HPLC analysis: $^1$H NMR (300 MHz, DMSO-$d_6$) NMR was consistent with the desired product.

Preparation 87

4-(4-(2-Amino-2-methylpropyl)phenoxy)benzamide

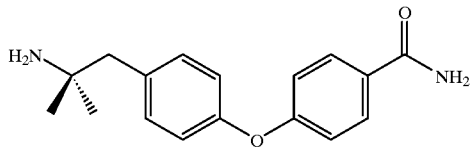

Aqueous 30% $H_2O_2$ (62.1 mL, 548 mmol) was added dropwise to a mixture of 4-(4-(2-amino-2-methylpropyl)phenoxy)benzonitrile (53.2 g, 200 mmol), $K_2CO_3$ (15.78 g, 114 mmol) and DMSO (270 mL) over 20 min while the temperature was held at 20° C. with a cooling bath. The mixture was stirred at this temperature for 1 h after the addition was complete, and then water (209 mL) was added slowly. The slurry was cooled in an ice bath with stirring for 1 h, and the product was then filtered, washed with water and dried in vacuo at 50° C. to yield 55.0 g (97%) of white solid. Analysis by HPLC indicated purity of >99%: $^1$H NMR (300 MHz, DMSO-$d_6$) NMR was consistent with the desired product.

Preparation 88

2-(4-(2-Amino-2-methylpropyl)phenoxy)-5-carbonitrilepyridine

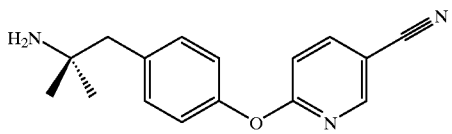

A mixture of 4-(2-amino-2-methylpropyl)phenol acetic acid salt (22.53 g, 100 mmol), powdered $K_2CO_3$ (34.55 g, 250 mmol) and DMAC (275 ml) was heated to 100° C. Toluene (94 ml) was added and the mixture slowly heated to reflux. The reflux temperature was raised by distillation of toluene and water until it reached 140° C. The mixture was then cooled to below 100° C. and 2-chloronicotinonitrile (13.86 g, 100 mmol) added with a toluene rinse (50 ml). The mixture was again heated to reflux and the reflux temperature raised to 140° C. as before. Then the water trap was filled with toluene and the reflux continued for 40 min., at which point an HPLC showed no 2-chloronicotinonitrile remained but the reaction was not complete. After cooling the reaction below reflux, additional 2-chloronicotinonitrile (0.63 g, 4.5 mmol) was added and reflux continued for 90 min. The reaction was cooled to room temperature and the solids filtered with a toluene wash. The filtrate was concentrated on a rotary evaporator to 41 g of syrup which was dissolved in EtOAc (200 ml). This solution was washed with water (200 ml) and the aqueous layer back-extracted with EtOAc (50 ml). The combined organic layers were washed with water (3×200 ml) and concentrated in vacuo to 26.93 g of solid, ~100% of theory. HPLC indicated 94.3% purity. $^1$H NMR (300 MHz, DMSO-$d_6$) was consistent with the desired product.

Preparation 89

Ethyl(4-[2-methyl-2-nitropropyl]phenoxy)ethanoate

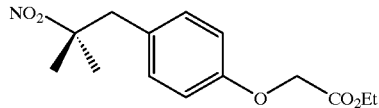

A mixture of 4-(2-methyl-2-nitropropyl)phenol (3.0 g, 15.4 mmol), ethylbromoacetate (2.04 mL, 17.0 mmol) and potassium carbonate (6.4 g, 46.2 mmol) was stirred at room temperature for 18 h. The reaction was concentrated in vacuo and the resulting residue partitioned between EtOAc and water. The layers were separated and the aqueous layer extracted with EtOAc (3×). The combined organic layers were washed with water (3×), brine, dried ($Na_2SO_4$), and concentrated in vacuo to a brown oil. The material was purified by flash chromatography over silica gel eluting with 5% MeOH/$CHCl_3$ to provide 4.22 g (97%) of a clear oil. NMR

Preparation 90

Ethyl(4-[2-amino-2-methylpropyl]phenoxy)ethanoate

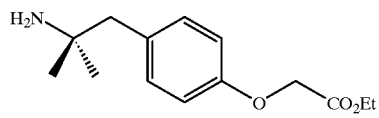

A solution of ethyl(4-[2-methyl-2-nitropropyl]phenoxy)ethanoate (3.6 g, 12.8 mmol) in ethanol (35 mL) was charged with platinum oxide (0.72 g) and hydrogenated on a Parr shaker using 60 psi of hydrogen for 72 h at room temperature. The catalyst was filtered and the solution concentrated in vacuo. The resulting residue was purified by flash chromatography over silica gel eluting with 5% MeOH/$CHCl_3$/$NH_3$ to provide 0.9 g (28%) of a clear oil. MS (FD+): m/z 251.

Preparation 91

4-(3-Hydroxy-3-methylbutyl)phenol

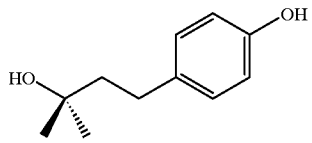

Methyl magnesium bromide (50.7ml, 0.15 mol, 3.0M in ether) was dissolved in anhydrous THF (140 ml) with stirring under a nitrogen atmosphere. A solution of (4-hydroxyphenyl)-4-butanone (10.0 g, 60.9 mmol) in anhydrous THF (60 ml) was then slowly introduced via dropwise addition; the resulting exotherm was controlled by the use of a cool water bath to keep the temperature below 30° C. The reaction mixture was allowed to stir at ambient temperature for 16 hours at which time it was quenched by the dropwise addition of concentrated $NH_4Cl$. The aqueous solution was extracted with ether (1×200 ml) and then acidified by the addition of 1.0N HCl (150 ml). The acidic aqueous suspension was extracted with ether (2×150 ml) and the organic layers combined and washed with a saturated solution of NaHCO₃, and then brine. The organic layer was concentrated in vacuo and the residue recrystallized from chloroform to produce a white solid (9.16 g, 83%). NMR, MS.

Preparation 92

4-(3-Benzoylamino-3-methylbutyl)phenol

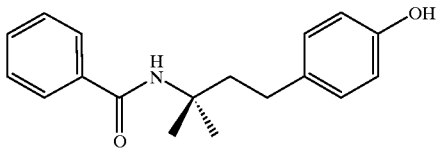

4-(3-Hydroxy-3-methylbutyl)phenol(7.5 g, 41.6 mmol) and benzonitrile (4.7 ml, 45.8 mmol, 1.1 eq.) were dissolved in acetic acid (50 ml) and concentrated H₂SO₄ (7.4 ml) was added dropwise slowly while stirring, causing a significant exotherm. After 20 minutes, the reaction mixture was cooled in an ice bath and neutralized with a saturated solution of Na₂CO₃. The aqueous suspension was extracted with ethyl acetate (2×100 ml) and the combined organic layers were washed with a saturated solution of NaHCO₃ (1×200 ml) and then with brine (1×100 ml). The organic extracts were dried with Na₂SO₄, filtered and concentrated in vacuo to produce a white solid. The solid was triturated in 3:1 toluene/ethyl acetate to produce a white solid (5.38 g, 45%). NMR, MS, EA Preparation 93

4-(3-Benzylamino-3-methylbutyl)phenol hydrochloride

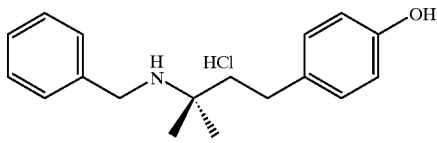

4-(3-Benzoylamino-3-methylbutyl)phenol (1.07 g, 3.77 mmol) was dissolved in anhydrous DMF (20 ml) and treated with a solution of borane-dimethyl sulfide complex (1.76 ml, 18.9 mmol, 5 eq., 10M in THF) with stirring under a nitrogen atmosphere. The reaction mixture was heated to 84° C. for four hours and then allowed to cool to ambient temperature. The solution was then quenched by slow addition of 1N Hcl and then returned to pH >10 by addition of solid NaHCO₃. The aqueous suspension was extracted with ethyl acetate (2×75 ml) and the organic layer then washed with brine. The organic solution was then dried with Na₂SO₄, filtered and concentrated in vacuo to produce an oily residue. The residue was redissolved in ether and converted to the hydrochloride salt by rapid addition of an excess of HCl 1.0M in ether. The resulting precipitate was filtered and dried to produce a white solid (938 mg, 81%). NMR, MS, EA.

Preparation 94

4-(3-Amino-3-methylbutyl)phenol hydrochloride

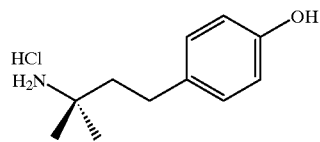

4-(3-Benzylamino-3-methylbutyl)phenol hydrochloride (3.84 g, 12.6 mmol) and 10% palladium on carbon (0.8 g) were suspended in methanol (95 ml) in a hydrogenation apparatus. The vessel was sealed and shaken for 16 hours at 50° C. and a 60 psi hydrogen atmosphere. The resulting suspension was filtered through Celite and concentrated in vacuo to yield a white solid (1.46 g, 54%). NMR, MS.

Preparation 95

4-(4-(3-Amino-3-methylbutyl)phenoxy)benzonitrile hydrochloride

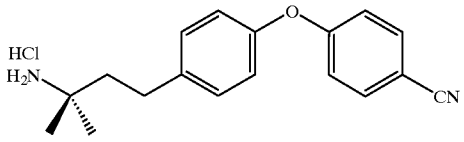

4-(3-Amino-3-methylbutyl)phenol hydrochloride (1.14 g, 5.3 mmol), 4-fluorobenzonitrile (0.77 g, 6.4 mmol, 1.2 eq.) and potassium carbonate (1.65 g, 11.6 mmol, 2.2 eq.) were suspended in N,N-dimethyl-acetamide (15 ml) and stirred for 16 hours at 110° C. After this time, the darkened mixture was allowed to cool to ambient temperature. The suspension was diluted with ethyl acetate (100 ml) and washed with 1N NaOH (2×100 ml). The organic layer was treated with 5N HCl (100 ml), producing a white precipitate at the biphasic interface. The solid material was filtered and dried, triturated with pentane and dried in vacuo for 14 hours to produce a white solid (1.04 g, 71%). NMR, MS Preparation 96

4-(4-(3-Amino-3-methylbutyl)phenoxy)benzamide

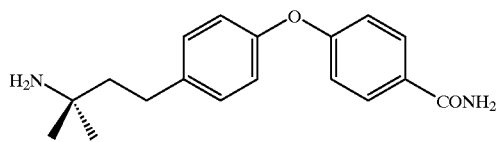

4-(4-(3-Amino-3-methylbutyl)phenoxy)benzonitrile hydrochloride (1.04 g, 32.8 mmol) was dissolved in DMSO (30 ml) and treated with potassium carbonate (0.68 g, 49.2 mmol, 1.5 eq.) with stirring. After 10 minutes, hydrogen peroxide (7 ml, 30% aqueous solution) was added dropwise slowly. The mixture was allowed to stir for 16 hours and then added to 300 ml of water, causing a white precipitate. The material was filtered and dried to give a white solid (908 mg, 93%). NMR, MS

Preparation 97

3,5-Dicarboethoxy-4-hydroxypyrazole

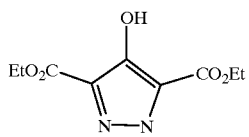

Sodium methoxide (18.9 g, 0.35 moles) was suspended in methanol (400 ml) at 5° C. Dimethylmalonate (46.2, 0.35 moles) and ethyldiazoacetate (20 g, 0.175 moles) was added quickly and the reaction stirred at room temperature for 72 hours. The reaction was cooled to 5° C. and hydrochloric acid (70 ml of 5M) added; followed by 500 ml of water. The pH of the reaction was adjusted to 7 with sodium bicarbonate and the solids (22 g, 63%) collected by filtration. EA, MS

Preparation 98

4-Hydroxypyrazole

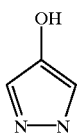

3,5-Dicarboxy-4-hydroxypyrazole (21.5 g, 0.11 moles) was suspended in concentrated hydrochloric acid (200 ml) and heated slowly to reflux. Solids slowly went into solution and gas was evolved. After heating overnight, the solvent was vacuum distilled at 6 mm/Hg up to pot temperature of 80° C. The product (5.02 g, 54%) sublimed out of the pot at 6 mm/Hg and 200° C. EA, MS, NMR

Preparation 99

4-t-Butyldimethylsilyloxypyrazole

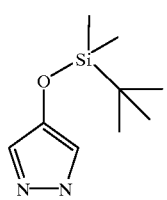

4-Hydroxypyrazole (1.16 g, 13.8 mmol) and imidazole (1.13 g, 16.6 mmol) were suspended in DMF (50 ml) under nitrogen and t-butyldimethylsilylchloride (2.3 g, 15.2 mmol) was added. After stirring 17 hours, the solvent was removed in vacuo and the residue treated with water containing 4.5 g of potassium carbonate. The mixture was extracted with two portions of chloroform and the organic layer dried over sodium sulfate. The solvent was removed in vacuo to yield product (2.58 g, 94%). NMR

Preparation 100

1-Benzyl-4-t-butyldimethylsilyloxypyrazole

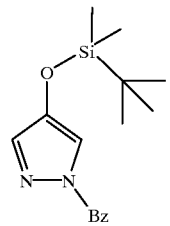

2-t-Butyldimethylsilyloxypyrazole (2.5 g, 12.6 mmol), benzylbromide (2.16 g, 12.6 mmol), and potassium carbonate (3.5 mg, 22.5 mmol) was dissolved in DMF (40 ml). The mixture was stirred 17 hours and the solvent removed in vacuo. The residue was taken up in water and extracted with portions of chloroform. The organic layer was washed with brine and dried over sodium sulfate. The solvent was removed and the crude material purified by column chromatography (silica gel, chloroform) to yield product (3.17 g, 61%). EA, MS, NMR

Preparation 101

1-Trityl-4-t-butyldimethylsilyloxypyrazole

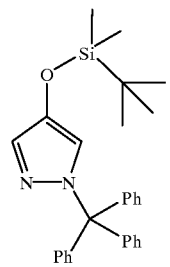

2-t-Butyldimethylsilyloxypyrazole (16.4 g, 0.0827 mol) and trityl chloride were reacted substantially in accordance with preparation 100 to yield product (3.5 g). NMR, MS.

Preparation 102

1-Benzyl-4-hydroxypyrazole

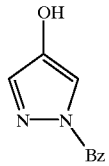

1-Benzyl-4-t-butyldimethylsilyloxypyrazole (3.0 g, 10.4 mmol) was dissolved in THF (20 ml) and tetrabutylammonium fluoride (52 ml of 1M solution in THF) was added. The reaction was stirred overnight and the solvent removed in vacuo. The residue was dissolved in water and extracted into diethylether. The organics dried over sodium sulfate, and the ether removed in vacuo. The residue purified by column chromatography (silica gel, chloroform→2% methanol/chloroform) to yield product (0.63 g, 35%). MS

Preparation 103

1-Trityl-4-hydroxypyrazole

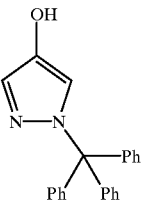

1-Trityl-4-t-butyldimethylsilyloxypyrazole (4.0 g, 9.1 mmol) was reacted substantially in accordance with preparation 102 to yield product (3.5 g). NMR, MS.

Preparation 104

1-Trityl-4-hydroxypyrazole

4-Hydroxypyrazole (0.5 g, 6 mmol) was dissolved in 50 ml of acetonitrile; triethylamine (3.3 ml, 4 equiv.) and chlorotrimethylsilane (0.9 ml, 1.2 equiv.) was added at room temperature. After two hours of stirring, chlorotriphenylmethane (1.66 g, 1 equiv.) was added and the mixture stirred 16 hours. The mixture was heated to reflux for 30 minutes and the solvent removed in vacuo. The residue was treated with water and sodium bicarbonate powder and then was extracted into ethylacetate, washed with brine, and dried over sodium sulfate. The solvent was once again removed and the residue purified by column chromatography (1:1, hexanes-ethylacetate) to yield product (1.4 g, 73%). NMR, EA, MS. Alternatively the product can be purified by crystallization from methanol instead of through chromatography.

Preparation 105

(s)-1-Benzyl-4-glycidylpyrazole

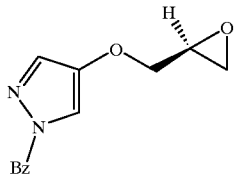

1-Benzyl-4-hydroxypyrazole (2 g, 11.5 mmol), potassium carbonate(3.2 g, 23 mmol), and (2s)-glycidyl-3-nitrobenzenesulfonate (2.98 g, 11.5 mmol) were slurried in actone (300 ml) at reflux for 17 hours. The acetone was removed in vacuo, the residue extracted from brine with chloroform, and dried over sodium sulfate. The solvent was removed again and the residue purified by column chromatography (silica gel, chloroform→1% methanol/chloroform) to yield product (1.8 g, 68%). MS, NMR.

Preparation 106

(s)-1-Trityl-4-glycidylpyrazole

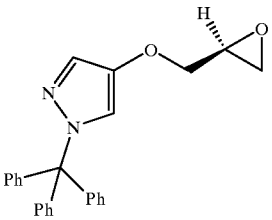

1-Trityl-4-hydroxypyrazole (2.5 g, 7.66 mmol) was reacted substantially in accordance with preparation 105 to yield product (1.75 g). NMR, MS, EA.

Example 1 is a combinatorial chemistry parallel method for preparing compounds of the present invention in matrix fashion.

EXAMPLE 1

A 5×8 grid of 4 mL screw cap vials is arranged. To each of the eight rows of vials in the grid is added 33 mmol of ketone (from preparations 1–14 and 25–92, or commercially available), one ketone per row, as a stock solution in methanol (0.5M, 65 ml). If solubility is a problem, acetonitrile/methanol or DMF is used. To each column of vials in the grid is added 50 mmol of amine hydrochloride (from scheme III), one amine hydrochloride per column, as a stock solution in methanol (0.5M, 100 ml). To each vial is then added resin VIII (18–20 mg), 1.01 meq/g, 70–90 meq base). Teflon® lined caps are then placed on each vial. The slurries are then shaken for 24 hours, at which time each vial is treated with approximately 30 mg (2.5 mmol $BH_4^-$/g resin, 75 mmol) of Amberlite® IRA400 borohydride resin (Aldrich Chemicals). The caps are replaced, and the vials are shaken for an additional 24 hours, then 150 ml methylene chloride and 40 mg (1 mmol/g resin, 0.4 mmol) polystyrene-linked benzaldehyde resin (Frechet, J. M.; Schuerch, C. J. Am. Chem. Soc. 1971, 93, 492.) in order to scavenge excess primary amine starting material are added to the vial, and the slurry is shaken for 1 day. Each vial is then filtered through a cotton plug. The residual resin is rinsed with three small portions of methanol (approximately 200 μl total). The resulting solutions are then treated with 20 μl of conc. HCl (120 μmol) to ensure formation of the HCl salt of the product amine, then each vial is diluted to a volume of approximately 4 mL, and 1 mL of each solution is transferred to a tared 4 mL screw cap vial. This solution is allowed to evaporate in a fume hood under an air stream until dry, then placed in a vacuum oven for 24 hours at room temperature. The resulting residues are then weighed and submitted directly for testing with no further purification. The bulk of the material (75%) is similarly evaporated.

The following matrices list additional examples 2–201. These compounds can be prepared using combinatorial chemistry parallel array synthesis techniques in accordance with the present invention. All reaction conditions are the same from example to example and in substantial accordance with Scheme 2 and Example 1. A scaffold for each plate is the same and is depicted at the top of the 5×8 matrix. The scaffold means the invariant region (i.e. the core) of the compounds which are members of the combinatorial chemistry library. The variable functional groups are illustrated in the rows and columns. The ketones and the amines depicted on each plate are prepared in accordance with the schemes and preparations described herein or by techniques known in the art.

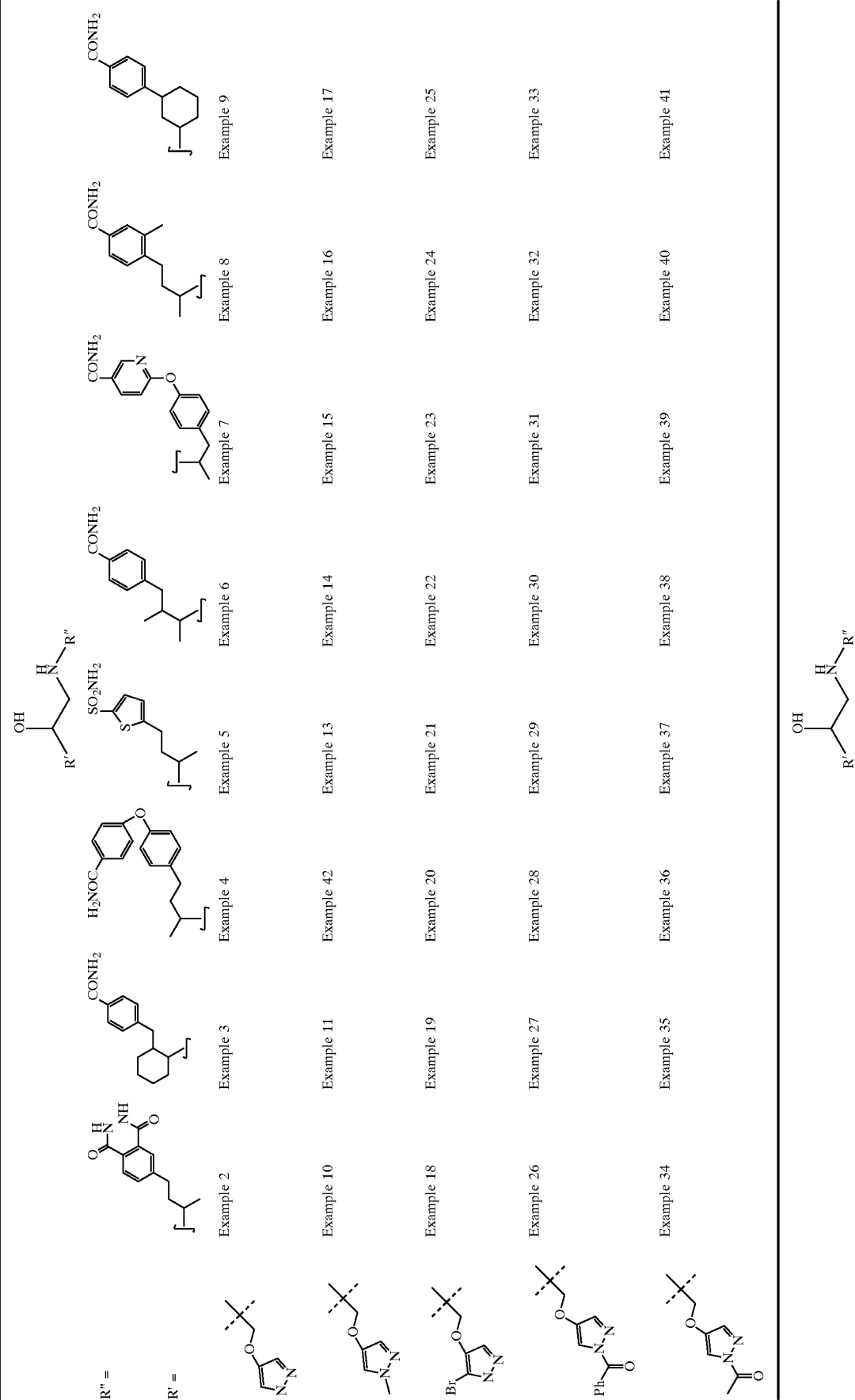

-continued
| R″ = | 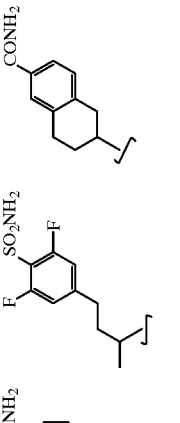 | 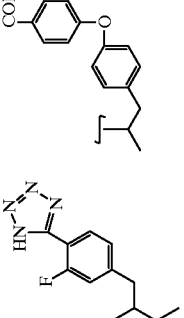 | 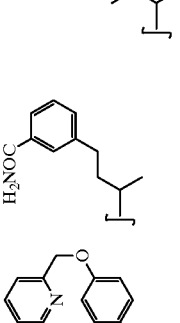 | 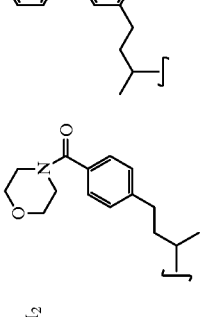 | 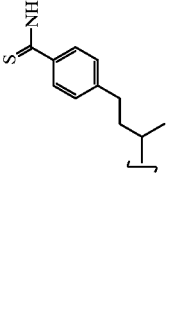 |  |  |  |
|---|---|---|---|---|---|---|---|---|
| R′ = | | | | | | | | |
| 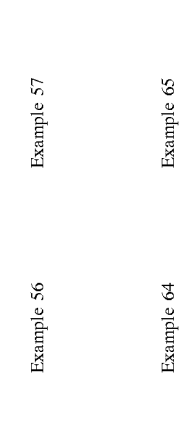 | Example 42 | Example 43 | Example 44 | Example 45 | Example 46 | Example 47 | Example 48 | Example 49 |
| 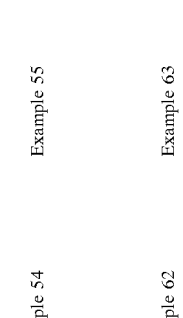 | Example 50 | Example 51 | Example 52 | Example 53 | Example 54 | Example 55 | Example 56 | Example 57 |
| 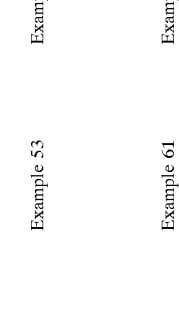 | Example 58 | Example 59 | Example 60 | Example 61 | Example 62 | Example 63 | Example 64 | Example 65 |
| 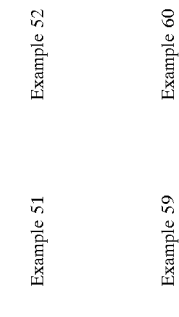 | Example 66 | Example 67 | Example 68 | Example 69 | Example 70 | Example 71 | Example 72 | Example 73 |
| 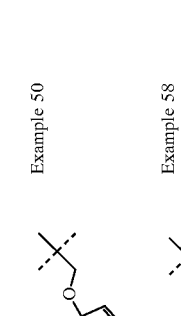 | Example 74 | Example 75 | Example 76 | Example 77 | Example 78 | Example 79 | Example 80 | Example 81 |

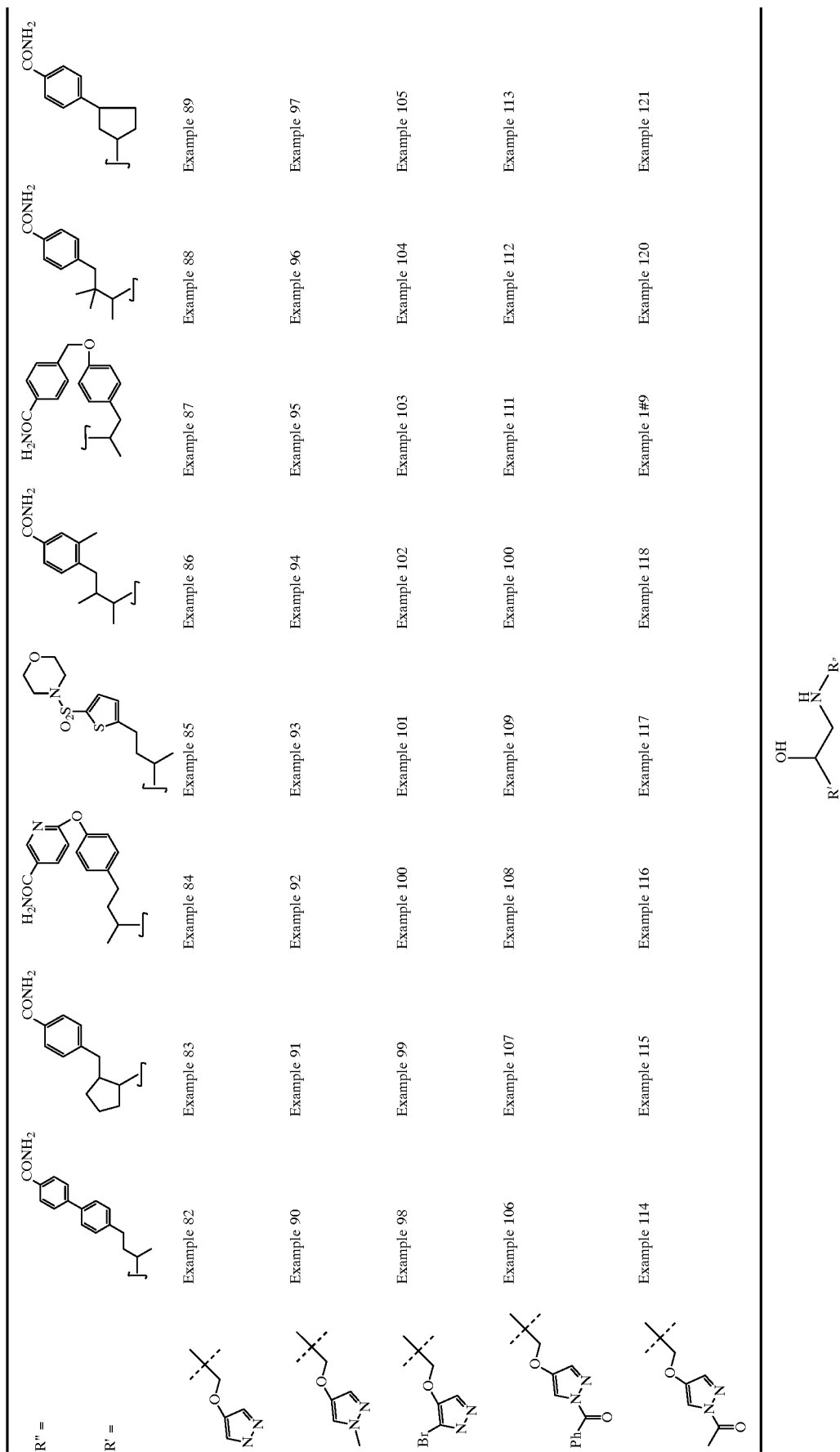

-continued

| R'' = | 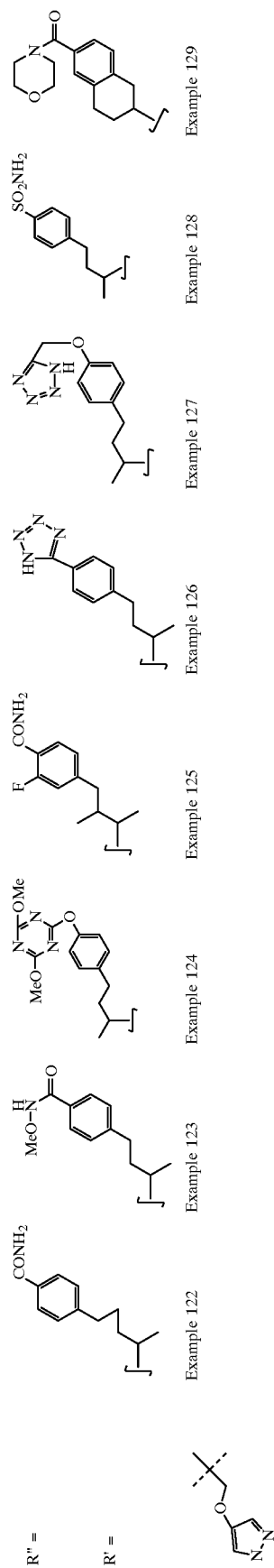 | | | | | | | |
|---|---|---|---|---|---|---|---|---|
| R' = | | CONH₂ phenyl-alkyl | MeO-NH-C(=O)-phenyl-alkyl | (MeO,OMe)N=C-O-phenyl-alkyl | F,CONH₂-phenyl-alkyl | tetrazolyl-phenyl-alkyl | tetrazolyl-O-CH₂-phenyl-alkyl | SO₂NH₂-phenyl-alkyl | morpholino-C(=O)-naphthyl |
| pyrazolyl-O-CH₂ | | Example 122 | Example 123 | Example 124 | Example 125 | Example 126 | Example 127 | Example 128 | Example 129 |
| N-methyl pyrazolyl-O-CH₂ | | Example 130 | Example 131 | Example 132 | Example 133 | Example 134 | Example 135 | Example 136 | Example 137 |
| Br-pyrazolyl-O-CH₂ | | Example 138 | Example 139 | Example 140 | Example 141 | Example 142 | Example 143 | Example 144 | Example 145 |
| Ph-C(=O)-pyrazolyl-O-CH₂ | | Example 146 | Example 147 | Example 148 | Example 149 | Example 150 | Example 151 | Example 152 | Example 153 |
| Ac-pyrazolyl-O-CH₂ | | Example 154 | Example 155 | Example 156 | Example 157 | Example 158 | Example 159 | Example 160 | Example 161 |

-continued

| R'' = | CONH₂ (phenyl-CHMe-CHMe-) | CONH₂ (cycloheptyl-CH₂-phenyl-) | HO₂C-phenyl-O-phenyl-CH₂-CHMe- | SO₂NH₂ (thienyl-CHMe-CHMe-) | CONH₂ (phenyl-CMe₂-CHMe-) | MeOHNOC-phenyl-O-phenyl-CH₂-CHMe- | CN (phenyl-cyclohexyl-) | CONH₂ (phenyl-cyclohexyl-) |
|---|---|---|---|---|---|---|---|---|
| R' = pyrazolyl-O-CMe₂-CH₂- | Example 162 | Example 163 | Example 164 | Example 165 | Example 166 | Example 167 | Example 168 | Example 169 |
| N-methyl-pyrazolyl-O-CMe₂-CH₂- | Example 170 | Example 171 | Example 172 | Example 173 | Example 174 | Example 175 | Example 176 | Example 177 |
| Br-pyrazolyl-O-CMe₂-CH₂- | Example 178 | Example 179 | Example 180 | Example 181 | Example 182 | Example 183 | Example 184 | Example 185 |
| Ph-CO-pyrazolyl-O-CMe₂-CH₂- | Example 186 | Example 187 | Example 188 | Example 189 | Example 190 | Example 191 | Example 192 | Example 193 |
| Ac-pyrazolyl-O-CMe₂-CH₂- | Example 194 | Example 195 | Example 196 | Example 197 | Example 198 | Example 199 | Example 200 | Example 201 |

EXAMPLE 202

(S)1-Benzyl-4-(3-[N-(3-[4-(4-carbamoylphenoxy)phenyl]-1,1-dimethylpropyl)amino]-2-hydroxypropoxy)pyrazole

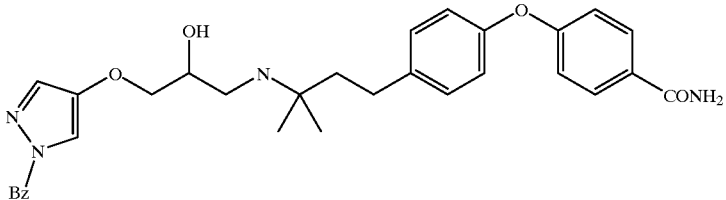

(s)-1-Benzyl-4-glycidylpyrazole (1.75 g, 7.6 mmol) and 4-(4-(3-Amino-3-methylbutyl)phenoxy)benzamide (3.6 g, 12 mmol) were heated to 45° C. for 72 hours in 100 ml of ethanol. The solvent was removed in vacuo, the residue dissolved in chloroform and washed with brine and aqueous sodium bicarbonate. The organic layer was dried over sodium sulfate and the solvent removed. The residue was purified by column chromatography (chloroform→10% methanol/chloroform) to yield product (2.1 g, 52.5%). EA, MS, NMR.

EXAMPLE 203

(S)-4-(3-[N-(3-[4-(4-carbamoylphenoxy)phenyl]-1,1-dimethylpropyl)amino]-2-hydroxypropoxy)pyrazole

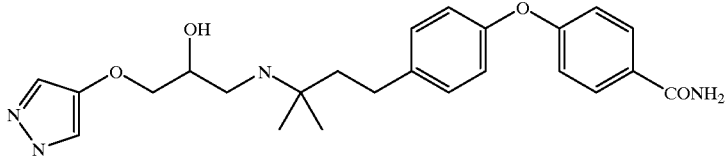

(S)1-Benzyl-4-(3-[N-(3-[4-(4-carbamoylphenoxy)phenyl]-1,1-dimethylpropyl)amino]-2-hydroxypropoxy)pyrazole (1.2 g) was treated with hydrogen and 20% palladium(II) hydroxide on carbon (1.2 g) in ethanol for 72 hours at 40° C. The reaction was filtered and the solvent removed in vacuo. The residue was purified by column chromatography (chloroform→25/5/1 chloroform/methanol/ammonium hydroxide) to yield product (0.316 g, 32%). MS(m+1) 439; EA: theory % C 65.73, % H 6.90, % N 12.78; found % C 66.00, % H 6.81, % N 12.95.

EXAMPLE 204

(S)-4-(3-[N-(3-[4-carbamoylphenyl]-1,1-dimethylpropyl)amino]-2-hydroxypropoxy)pyrazole

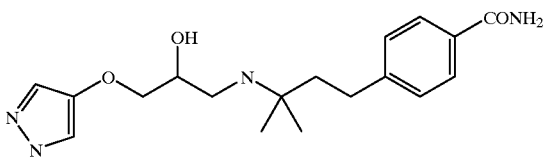

(s)-1-Trityl-4-glycidylpyrazole (1.7 G, 4.44 mmol) and 1,1-dimethyl-3-(4-carbamoylphenyl)propylamine (1.008 g, 4.9 mmol) were heated to reflux for 17 hours in 100 ml of ethanol. The solvent was removed in vacuo and the residue slurried in 25 ml of methanol and 50 ml of 1M hydrochloric acid and methanol added until a solution formed. After stirring at room temperature for 2 hours, the solvent was reduced in volume by 75% and the mixture made basic by addition of 1M sodium hydroxide. The aqueous phase was extracted with chloroform/methanol and THF. The combined organics were washed with brine and dried over sodium sulfate and the crude product purified by column chromatography (silica gel, chloroform/methanol/ammonium hydroxide: 89/10/1) to yield product (1.3 g, 85%). MS(m+1)347 EA: theory % C 62.4, % H 7.56, % N 16.17; found % C 62.89, % H 7.92, % N 15.01.

As previously noted, the compounds of the present invention are potent, selective $\beta_3$ receptor agonists. This pharmacological activity can be determined in the functional agonist $\beta_3$ assay.

Functional Agonists $\beta_3$ Assay

Cell Lines

The $h\beta_2$ DNA was expressed from a plasmid 57537 obtained from American Type Culture Collection. $h\beta_1$ and $h\beta_3$ adrenergic receptors were cloned from human genomic libraries using the polymerase chain reaction method with degenerate probes. Full length receptors were cloned, expressed and sequenced to verify identity according to published sequences ($h\beta_1$: T. Frielle et. al. (1993) *Molecular Pharmacology* 44: 264–270). These receptors were then expressed in the DXB-11 variant of CHO cells using a vector restoring tetrahydrofolate reductase and hygromycin resistance. Rat $\beta_3$ receptor expressing CHO cell line is known in the art. *Mol. Pharm.*, Vol 40, pp. 895–99 (1991). CHO cells were grown in 10% dialyzed FBS./high glucose DMEM/0.1% proline.

cAMP Assay

Cell membranes were harvested from the above cell line using hypotonic 25 mM Hepes (pH 7.4), 1 mM EDTA, 20 µg/mL leupeptin, 1 mM PMSF buffer with scraping followed by differential centrifugation. Membranes were incubated in 25 mM Tris (pH 7.6), 0.2% BSA, 2.6 mM Mg, 0.8 mM ATP, 0.1 mM GTP, 5 mM creatine phosphate, creatine kinase 50 U/mL, 0.2 mM IBMX at 32° C. Agonists were added and incubation continued for 15 m. cAMP produced was assayed using a fluorescent tracer-immuno assay method.

Intact cell assays were performed using suspended cells removed from culture flasks by trypsin treatment. Cells were preincubated with 0.5 mM IBMX at 37° C. Agonists were added and incubation continued for 15 m. Incubation was stopped by heating suspension in boiling water. cAMP or cGMP in these and the soleus incubations were assayed by RIA (Amersham).

The compounds of the invention are agonists of the $\beta_3$ receptor. Isoproterenol is accepted in the art as a non-selective $\beta_3$ agonist and is widely used as a comparator in evaluating the activity of compounds. See Trends in Pharm. Sci. 15: 3 (1994). In the $\beta_3$ assay, the compounds demonstrated at least 30%, preferably 50% and most preferably over 85% of isoproterenol's response at a single dose of 50 mmol. Dose response titrations on the agonists described reveal $EC_{50}$ values of <10 mM, preferably <1 mmol. In the functional assay, dose titration furnishes an $EC_{50}$ for isoproterenol of 1.1±0.5 $\mu$M.

When screened against the $\beta_1$ and $\beta_2$ receptors in the functional assay, dose titration experiments indicate that greatly reduced or no receptor stimulation is observed with the compounds of the invention. This is defined by measuring the intrinsic activity (maximal response achieved) as compared to isoproterenol. The claimed compounds of Formula I are selective $\beta_3$ receptor agonists and have an intrinsic activity of <3% of isoproterenol's response.

As agonists of $\beta_3$, the compounds are useful in treating conditions in a mammal in which the $\beta_3$ receptor has been demonstrated to have a role in pathology. The preferred mammal is a human. The relationship between modulating the $\beta_3$ receptor and treatment of diseases, such Type II diabetes and obesity, is well established in the art. Other conditions recognized in the art include: gastrointestinal disorders such as gastrointestinal motility, asthma, and depression. Thus, the present compounds are useful in the treatment of inflammatory bowel disease (Crohn's disease or ulcerative colitis), irritable bowel syndrome, non-specific diarrhoea and dumping syndrome.

In treating non-human mammals, the compounds of the present invention are useful for increasing weight gain and/or improving the feed utilization efficiency and/or weight gain and/or improving the feed utilization efficiency and/or increasing lean body mass and/or decreasing birth mortality rate and increasing post/natal survival rate of livestock.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients.

The pharmaceutical formulations of the present invention are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 mg to about 500 mg, more usually about 0.5 mg to about 200 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.05 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 mg compound per $cm^2$ of an affected tissue. Preferably, the applied amount of compound will range from about 30 to about 300 $mg/cm^2$, more preferably, from about 50 to about 200 $mg/cm^2$, and, most preferably, from about 60 to about 100 $mg/cm^2$.

The following formulation example is illustrative only and is not intended to limit the scope of the invention in any way.

Formulation 1

Hard gelatin capsules are prepared using the following ingredients:

|  | Quantity (mg/capsule) |
| --- | --- |
| Active Ingredient | 25 |
| starch, dried | 425 |
| magnesium stearate | 10 |
| Total | 460 mg |

The above ingredients are mixed and filled into hard gelatin capsules in 460 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A compound represented by the following Structural Formula (I):

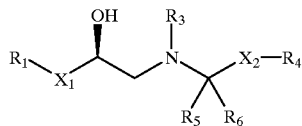   (I)

wherein:

$X_1$ is —OCH$_2$—, —SCH$_2$—, or a bond;

$R_1$ is a heterocycle of the formula:

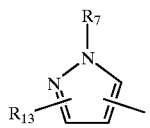

$R_2$ and $R_3$ are independently hydrogen, $C_1$–$C_4$ alkyl, or aryl;

$R_4$ is: 1) an optionally substituted heterocycle selected from the group consisting of pyrazolyl, pyrazolinyl, imidazolyl, isoxazolyl, triazolyl, tetrazolyl, oxazolyl, 1,3-dioxolonyl, thiazolyl, oxadiazolyl, thiadiazolyl, pyridinyl, pyrimidinyl, piperazinyl, morpholinyl, pyrazinyl, pyrrolidinyl, piperidinyl, oxazolidonyl, oxazolidinedionyl and imidazolidinonyl; or 2) a moiety selected from the group consisting of:

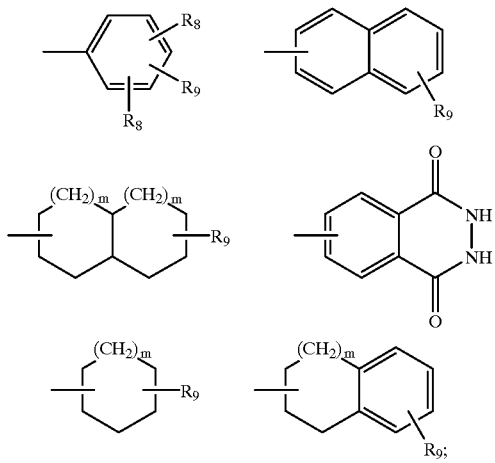

$X_2$ is a bond, or a 1 to 5 carbon straight or branched alkylene;

$R_5$ is hydrogen or $C_1$–$C_4$ alkyl;

$R_6$ is hydrogen or $C_1$–$C_4$ alkyl;

or $R_5$ and $R_6$ combine with the carbon to which each is attached to form a $C_3$–$C_6$ cycloalkyl;

or $R_6$ combines with $X_2$ and the carbon to which each is attached to form a $C_3$–$C_8$ cycloalkyl;

or $R_6$ combines with $X_2$, $R_4$, and the carbon to which each is attached to form:

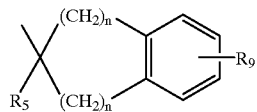

provided that $R_5$ is hydrogen;

$R_7$ is hydrogen, hydroxy, cyano, oxo, Co$_n$R$_2$, CONHR$_2$, $C_1$–$C_4$ alkyl, $C_1$–$C_4$ alkoxy, $C_1$–$C_4$ haloalkyl, $C_1$–$C_4$ optionally substituted alkyl, (CH$_2$)$_n$ aryl, (CH$_2$)$_n$heterocycle, (CH$_2$)$_n$ optionally substituted aryl, or (CH$_2$)$_n$ optionally substituted heterocycle;

$R_8$ is independently hydrogen, halo, or $C_1$–$C_4$ alkyl;

$R_9$ is halo, CN, OR$_{10}$, $C_1$–$C_4$ alkyl, $C_1$–$C_4$ haloalkyl, CO$_2$R$_2$, CONR$_{11}$R$_{12}$, CONH($C_1$–$C_4$ alkyl or $C_1$–$C_4$ alkoxy), SR$_2$, CSNHR$_2$, CSNR$_{11}$R$_{12}$, SO$_2$R$_2$, SOR$_2$, NR$_{11}$R$_{12}$, optionally substituted aryl, optionally substituted heterocycle, or $C_2$–$C_4$ alkenyl substituted with CN, CO$_2$R$_2$, or CONR$_{11}$R$_2$;

$R_{10}$ is $C_1$–$C_4$ alkyl, $C_1$–$C_4$ haloalkyl, (CH$_2$)$_n$C$_3$–C$_8$ cycloalkyl, (CH$_2$)$_n$aryl, (CH$_2$)$_n$heterocycle, (CH$_2$)$_n$C$_3$–C$_8$ optionally substituted cycloalkyl, (CH$_2$)$_n$ optionally substituted aryl, or (CH$_2$)$_n$ optionally substituted heterocycle;

$R_{11}$ and $R_{12}$ are independently hydrogen, $C_1$–$C_4$ alkyl, aryl, (CH$_2$)$_n$aryl, or combine with the nitrogen to which each is bound to form morpholinyl, piperidinyl, pyrrolidinyl, or piperazinyl;

$R_{13}$ is hydrogen, halo, aryl, or $C_1$–$C_4$ alkyl;

m is 0 or 1;

n is 0, 1, 2, or 3;

or a pharmaceutically acceptable salt thereof;

provided that when $R_4$ is

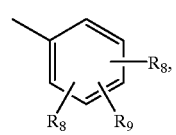

then $R_9$ is not $C_1$–$C_4$ alkyl or $C_1$–$C_4$ haloalkyl.

2. The compound of claim 1 wherein $R_4$ is represented by the following structural formula:

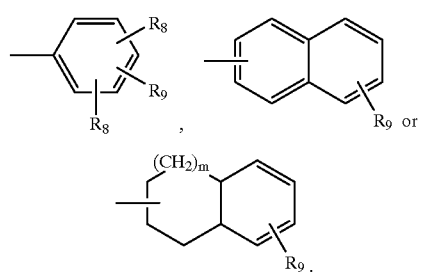

3. The compound of claim 2 wherein $R_4$ is represented by the following structural formula:

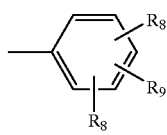

4. The compound of claim 3 wherein:

$R_7$ is —H;

$R_9$ is halo, CN, $OR_{10}$, $C_1$–$C_4$ alkyl, $CO_2R_2$, $CONR_{11}R_{12}$, $CONH(C_1$–$C_4$ alkyl or $C_1$–$C_4$ alkoxy), $SO_2R_2$, $SOR_2$ or optionally substituted aryl, optionally substituted heterocycle; and $R_{13}$ is H or halo.

5. The compound of claim 4 wherein $R_9$ is $CONR_{11}R_{12}$ or CN.

6. The compound of claim 4 wherein $R_9$ is —$OR_{10}$.

7. The compound of claim 6 wherein $R_{10}$ is $(CH_2)_nC_3$–$C_8$ cycloalkyl, $(CH_2)_n$aryl, $(CH_2)_n$heterocycle, said aryl, $C_3$–$C_8$ cycloalkyl, or heterocycle being optionally substituted.

8. A compound represented by the following Structural Formula (I):

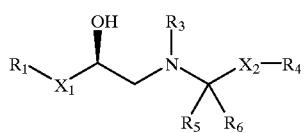
(I)

wherein:

$X_1$ is —$OCH_2$—, —$SCH_2$—, or a bond;

$R_1$ is a heterocycle of the formula:

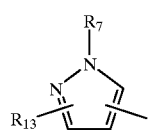

$R_2$ and $R_3$ are independently hydrogen, $C_1$–$C_4$ alkyl, or aryl;

$R_4$ is: 1) an optionally substituted heterocycle selected from the group consisting of pyrazolyl, pyrazolinyl, imidazolyl, isoxazolyl, triazolyl, tetrazolyl, oxazolyl, 1,3-dioxolonyl thiazolyl, oxadiazolyl, thiadiazolyl, pyridinyl, pyrimidinyl, piperazinyl, morpholinyl, pyrazinyl, pyrrolidinyl, piperidinyl, oxazolidonyl, oxazolidinedionyl and imidazolidinonyl; or 2) a moiety selected from the group consisting of:

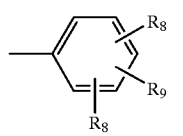 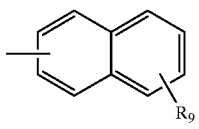

-continued

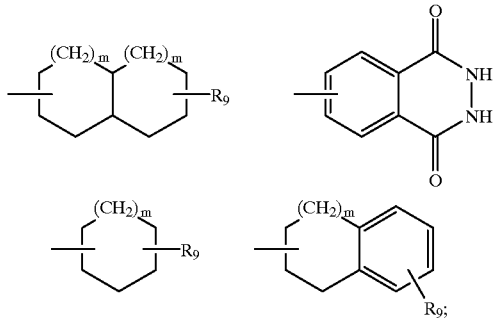

$X_2$ is a bond, or a 1 to 5 carbon straight or branched alkylene;

$R_5$ is hydrogen or $C_1$–$C_4$ alkyl;

$R_6$ is hydrogen or $C_1$–$C_4$ alkyl;

or $R_5$ and $R_6$ combine with the carbon to which each is attached to form a $C_3$–$C_6$ cycloalkyl;

or $R_6$ combines with $X_2$ and the carbon to which each is attached to form a $C_3$–$C_8$ cycloalkyl;

$R_7$ is hydrogen, hydroxy, cyano, oxo, $Co_nR_2$, $CONHR_2$, $C_1$–$C_4$ alkyl, $C_1$–$C_4$ alkoxy, $C_1$–$C_4$ haloalkyl, $C_1$–$C_4$ optionally substituted alkyl, $(CH_2)_n$ aryl, $(CH_2)_n$heterocycle, $(CH_2)_n$ optionally substituted aryl, or $(CH_2)_n$ optionally substituted heterocycle;

$R_8$ is independently hydrogen, halo, or $C_1$–$C_4$ alkyl;

$R_9$ is halo, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNHR_2$, $CSNR_{11}R_{12}$, $SO_2R_2$, $SOR_2$, $NR_{11}R_{12}$, optionally substituted aryl, optionally substituted heterocycle, or $C_2$–$C_4$ alkenyl substituted with CN, $CO_2R_2$, or $CONR_{11}R_{12}$;

$R_{10}$ is $C_1$–$C_4$ alkyl, $C_1$–$C_4$ haloalkyl, $(CH_2)_nC_3$–$C_8$ cycloalkyl, $(CH_2)_n$aryl, $(CH_2)_n$heterocycle, $(CH_2)_nC_3$–$C_8$ optionally substituted cycloalkyl, $(CH_2)_n$ optionally substituted aryl, or $(CH_2)_n$ optionally substituted heterocycle;

$R_{11}$ and $R_{12}$ are independently hydrogen, $C_1$–$C_4$ alkyl, aryl, $(CH_2)_n$aryl, or combine with the nitrogen to which each is bound to form morpholinyl, piperidinyl, pyrrolidinyl, or piperazinyl;

$R_{13}$ is hydrogen, halo, aryl, or $C_1$–$C_4$ alkyl;

m is 0 or 1;

n is 0, 1, 2, or 3;

or a pharmaceutically acceptable salt thereof;

provided that when $R_4$ is

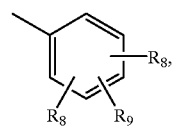

phenyl then $R_9$ is not $C_1$–$C_4$ alkyl or $C_1$–$C_4$ haloalkyl.

9. A compound represented by the following structural Formula:

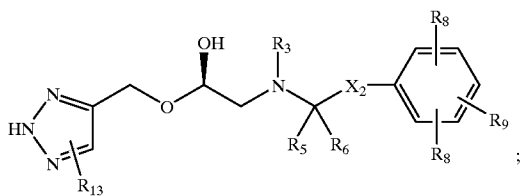

wherein:
$X_2$ is —CH$_2$—, —CH$_2$CH$_2$— or —CH$_2$CH$_2$CH$_2$—;
$R_2$ is hydrogen, $C_1$–$C_4$ alkyl, or aryl;
$R_3$ is —H or —CH$_3$;
$R_5$ and $R_6$ are both hydrogen or methyl;
$R_8$ is independently hydrogen, halo, or $C_1$–$C_4$ alkyl;
$R_9$ is —OR$_{10}$;
$R_{10}$ is aryl optionally substituted with CONR$_{11}$R$_{12}$, CN, CO$_2$R$_2$, or NR$_2$SO$_2$R$_2$ or pyridyl optionally substituted with CONR$_{11}$R$_{12}$, CN, CO$_2$R$_2$, or NR$_2$SO$_2$R$_2$;
$R_{11}$, and $R_{12}$, are independently hydrogen, $C_1$–$C_4$ alkyl, aryl, (CH$_2$)$_n$aryl, or combine with the nitrogen to which each is bound to form morpholinyl, piperidinyl, pyrrolidinyl, or piperazinyl; and
$R_{13}$ is —H or halo.

10. The compound of claim 8 wherein the compound is represented by the following structural formula:

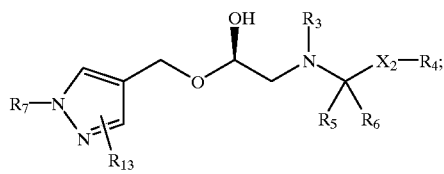

wherein:
$R_3$ is —H or —CH$_3$;
$R_5$ and $R_6$ are both hydrogen or methyl; and
$X_2$ is —CH$_2$—, —CH$_2$CH$_2$— or —CH$_2$CH$_2$CH$_2$—.

11. A method of stimulating the β3 receptors in a mammal which comprises administering to a mammal in need thereof a pharmaceutically effective amount of the compound of claim 8.

12. The method of claim 11 wherein the mammal is being treated for obesity or Type II diabetes.

13. The method of claim 12 wherein the compound is represented by the following structural formula:

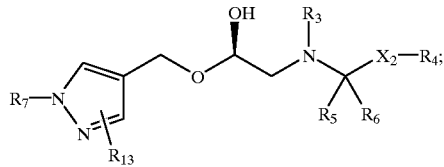

wherein:
$R_3$ is —H or —CH$_3$;
$R_5$ and $R_6$ are both hydrogen or methyl; and
$X_2$ is —CH$_2$—, —CH$_2$CH$_2$— or —CH$_2$CH$_2$CH$_2$—.

14. The method of claim 13 wherein $R_4$ is represented by the following structural formula:

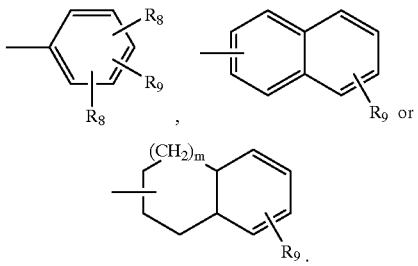

15. The method of claim 14 wherein $R_4$ is represented by the following structural formula:

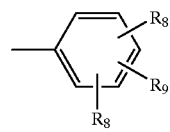

16. The method of claim 15 wherein:
$R_7$ is —H;
$R_9$ is halo, CN, OR$_{10}$, $C_1$–$C_4$ alkyl, CO$_2$R$_2$, CONR$_{11}$R$_{12}$, CONH($C_1$–$C_4$ alkyl or $C_1$–$C_4$ alkoxy), SO$_2$R$_2$, SOR$_2$ or optionally substituted aryl, optionally substituted heterocycle; and
$R_{13}$ is H or halo.

17. The method of claim 16 wherein $R_9$ is CONR$_{11}$R$_{12}$ or CN.

18. The method of claim 16 wherein $R_9$ is —OR$_{10}$.

19. The method of claim 18 wherein $R_{10}$ is (CH$_2$)$_n$C$_3$–C$_8$ cycloalkyl, (CH$_2$)$_n$aryl, (CH$_2$)$_n$heterocycle, said aryl, $C_3$–$C_8$ cycloalkyl, or heterocycle being optionally substituted.

20. The method of claim 19 wherein $R_{10}$ is aryl optionally substituted with CONR$_{11}$R$_{12}$, CN, CO$_2$R$_2$, or NR$_2$SO$_2$R$_2$ or pyridyl optionally substituted with CONR$_{11}$R$_{12}$, CN, CO$_2$R$_2$, or NR$_2$SO$_2$R$_2$.

21. A method of stimulating the β3 receptors in a mammal which comprises administering to a mammal in need thereof a pharmaceutically effective amount of the compound of claim 10.

22. The method of claim 21 wherein the mammal is being treated for obesity or Type II diabetes.

23. The method of claim 22 wherein the compound is represented by the following structural formula:

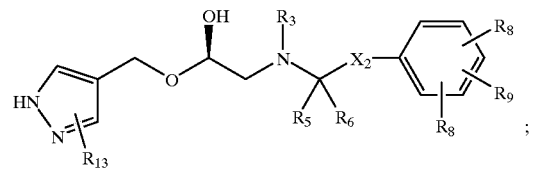

wherein:
$R_3$ is —H or —CH$_3$;
$R_5$ and $R_6$ are both hydrogen or methyl;
$X_2$ is —CH$_2$—, —CH$_2$CH$_2$— or —CH$_2$CH$_2$CH$_2$—;
$R_9$ is —NR$_2$SO$_2$R$_2$; and
$R_{13}$ is hydrogen or halo.

* * * * *